(12) United States Patent
Wilsey

(10) Patent No.: US 11,357,756 B2
(45) Date of Patent: Jun. 14, 2022

(54) ANESTHETIC COMPOSITIONS AND METHODS COMPRISING IMIDAZOLINE COMPOUNDS

(71) Applicant: Warsaw Orthopedic, Inc., Warsaw, IN (US)

(72) Inventor: Jared T. Wilsey, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 108 days.

(21) Appl. No.: 15/875,729

(22) Filed: Jan. 19, 2018

(65) Prior Publication Data

US 2018/0207133 A1    Jul. 26, 2018

Related U.S. Application Data

(60) Provisional application No. 62/448,726, filed on Jan. 20, 2017.

(51) Int. Cl.
*A61K 31/4164* (2006.01)
*A61P 29/00* (2006.01)
(Continued)

(52) U.S. Cl.
CPC ........ *A61K 31/4168* (2013.01); *A61K 9/0019* (2013.01); *A61K 9/0024* (2013.01);
(Continued)

(58) Field of Classification Search
CPC .......................... A61K 31/4168; A61K 9/0019
See application file for complete search history.

(56) References Cited

U.S. PATENT DOCUMENTS 6,534,081 B2   3/2003   Goldenheim et al.
6,921,541 B2   7/2005   Chasin et al.
(Continued)

FOREIGN PATENT DOCUMENTS

CN    104523683    5/2017
WO    2006109177   10/2006
(Continued)

OTHER PUBLICATIONS

Tran, et al., A randomized comparison between subepineural and conventional ultrasound-guided popliteal sciatic nerve block, Regional Anesthesia and Pain Medicine, vol. 36, No. 6, Dec. 2011 (retrieved on Feb. 23, 2018). Retrieved from the Internet: <URL:https://www.ncbi.nlm.nih.gov/pubmed/22005661>, abstract, 2 pages.
(Continued)

*Primary Examiner* — Brian Gulledge
(74) *Attorney, Agent, or Firm* — Sorell, Lenna & Schmidt, LLP; William D. Schmidt, Esq.

(57) ABSTRACT

Effective implantable medical devices and methods for reducing and treating acute pain by providing local anesthesia and nerve blockade using an imidazoline compound, such as clonidine are provided. In some embodiments, there is an injectable pharmaceutical composition comprising a therapeutically effective amount of imidazoline compound in a liquid pharmaceutical carrier, where the imidazoline compound provides local anesthesia and nerve block to the target tissue site which is a dorsal root ganglion, peripheral nerve fiber and/or peripheral nerve root.

7 Claims, 21 Drawing Sheets

(51) Int. Cl.
*A61K 31/4168* (2006.01)
*A61K 9/14* (2006.01)
*A61P 23/00* (2006.01)
*A61K 9/00* (2006.01)
*A61K 9/20* (2006.01)
*A61K 9/127* (2006.01)

(52) U.S. Cl.
CPC .............. *A61K 9/127* (2013.01); *A61K 9/14* (2013.01); *A61K 9/204* (2013.01); *A61P 23/00* (2018.01)

(56) References Cited

U.S. PATENT DOCUMENTS

| | | | |
|---|---|---|---|
| 7,589,057 | B2 | 9/2009 | Chang et al. |
| 8,114,437 | B2 | 2/2012 | Rohloff et al. |
| 8,557,273 | B2 | 10/2013 | McDonald et al. |
| 8,617,583 | B2 * | 12/2013 | King .................. A61K 9/0024 424/422 |
| 8,623,396 | B2 | 1/2014 | Gray et al. |
| 8,629,172 | B2 | 1/2014 | McKay et al. |
| 8,946,277 | B2 | 2/2015 | Zanella et al. |
| 8,999,368 | B2 * | 4/2015 | McDonald ........... A61K 9/0024 424/426 |
| 9,211,285 | B2 | 12/2015 | McKay et al. |
| 9,301,946 | B2 | 4/2016 | Wilsey et al. |
| 9,358,223 | B2 * | 6/2016 | King .................. A61K 9/0019 |
| 9,556,333 | B2 * | 1/2017 | Clay .......................... C08J 3/00 |
| 9,585,872 | B2 * | 3/2017 | Zanella ................ A61K 9/0024 |
| 9,610,243 | B2 * | 4/2017 | Clay .................... A61K 9/0085 |
| 9,763,917 | B2 * | 9/2017 | Zanella ................ A61K 9/0024 |
| 9,833,548 | B2 * | 12/2017 | McKay ................ A61K 9/0024 |
| 2003/0022926 | A1 | 1/2003 | Lavand'Homme |
| 2003/0069318 | A1 | 4/2003 | Dang et al. |
| 2003/0152637 | A1 | 8/2003 | Chasin et al. |
| 2003/0185873 | A1 * | 10/2003 | Chasin ................ A61K 31/715 424/426 |
| 2005/0119340 | A1 | 6/2005 | Anderson et al. |
| 2011/0207753 | A1 | 8/2011 | Woolf et al. |
| 2012/0142648 | A1 * | 6/2012 | Biggs ................... A61K 9/0024 514/171 |
| 2012/0142649 | A1 | 6/2012 | Gray et al. |
| 2013/0041330 | A1 | 2/2013 | Matsudo et al. |
| 2015/0374665 | A1 | 12/2015 | Hobot et al. |
| 2016/0158405 | A1 * | 6/2016 | Denyer ............... A61L 24/0015 424/450 |

FOREIGN PATENT DOCUMENTS

| | | | |
|---|---|---|---|
| WO | 2007115408 | 10/2007 | |
| WO | WO-2009100441 A2 * | 8/2009 | .......... A61K 9/1647 |
| WO | 2009129460 | 10/2009 | |
| WO | 2013151796 | 10/2013 | |

OTHER PUBLICATIONS

Oklahoma Pain Management, Relieve Chronic Osteoarthritis Pain of the Knee, Jan. 19, 2016 (retrieved on Feb. 23, 2018). Retrieved from the Internet: <URL:https://web.archive.org/web/20160119004238/ http://backpainok.com/genicular-knee-block/>, entire document, 4 pages.
International Search Report and Written Opinion for PCT/US2018/ 014506, the counterpart application, dated Mar. 8, 2018, 12 pages.
Wolff, M., et al. Clonidine reduces the excitability of spinal dorsal horn neurones. British Journal of Anaesthesia, vol. 98, Issue No. 3, Mar. 2007, pp. 353-361.
European Patent Office—Supplementary European Search Report EP 18 74 2220, Date of completion of search Jun. 24, 2020.

* cited by examiner

ANESTHETIC COMPOSITIONS AND METHODS COMPRISING IMIDAZOLINE COMPOUNDS

CROSS REFERENCE TO RELATED APPLICATIONS

This application claims priority to U.S. Provisional Application Ser. No. 62/448,726 filed on Jan. 20, 2017, the entire contents of which is incorporated herein by reference in its entirety.

BACKGROUND

Pain relief is of prime importance to anyone treating patients undergoing surgery. Proper pain relief imparts significant physiological and psychological benefits to the patient. Not only does effective pain relief mean a smoother, more pleasant post-operative course (e.g., mood, sleep, quality of life, etc.) but also an earlier discharge from medical, surgical and outpatient facilities.

Pain serves a biological function. It often signals the presence of damage or disease within the body and is often accompanied by inflammation (redness, swelling, and/or burning). In the case of acute pain, for example, post-operative pain, it may be a result of the surgery, or other treatments such as, for example, management of acute pain following burns or non-surgical trauma. Inadequate treatment of acute pain can lead to chronic pain and nociceptive sensitization (allodynia) which could potentially cause a dependency on centrally acting analgesics. The goal for acute pain, for example, post-operative pain management, is to reduce or eliminate pain and discomfort with medication that causes minimum or no side effects with a minimum or no dependency of the medication after treatment.

The site of the surgery has a profound effect upon the degree of post-operative pain a patient may suffer. In general, operations on the thorax and upper abdomen are more painful than operations on the lower abdomen, which in turn are more painful than peripheral operations on the limbs. However, any operation involving a body cavity, large joint surfaces, the spine or deep tissues should be regarded as painful. In particular, operations on the thorax or upper abdomen may produce widespread changes in pulmonary function, an increase in abdominal muscle tone and an associated decrease in diaphragmatic function. The result will be an inability to cough and clear secretions, which may lead to lung collapse and pneumonia. Prolonged pain can reduce physical activity and lead to venous stasis and an increased risk of deep vein thrombosis and consequently pulmonary embolism. In addition, there can be widespread effects on gut and urinary tract motility, which may lead in turn to post-operative ileus, nausea, vomiting and urinary retention. These problems are unpleasant for the patient and may prolong hospital stay. Many patients that experience moderate to severe post-operative pain, post-traumatic pain and burning pains, often require pain control at least in the first 3 days after trauma or surgery.

One known class of pharmaceuticals to treat acute pain, for example, post-operative pain, is opioids. This class of compounds is well-recognized as being among the most effective type of drugs for controlling post-operative pain. Unfortunately, because opioids are administered systemically, the associated side effects raise significant concerns, including disabling the patient, depressing the respiratory system, constipation, and psychoactive effects such as sedation and euphoria, thereby instituting a hurdle to recovery and regained mobility. Further, because of these side-effects, physicians typically limit the administration of opioids following surgery. Thus, it would be preferable to use non-narcotic drugs that deliver direct, localized pain control at a surgical site.

Imidazoline compounds, such as clonidine, are a class of compounds which are known and widely recognized by the medical profession. Clonidine has an imidazoline structure and in particular is known as an antihypertensive agent that acts as an agonist on the alpha-2-adrenergic receptor and as a neural receptor agonist. In general, clonidine, also referred to as 2,6-dichloro-N-2-imidazolidinyldenebenzenamine ($C_9H_9Cl_2N_3$) may be represented by the following chemical structure:

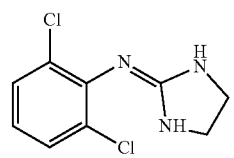 [SMILES: Clc1cccc(Cl)c1N=C1NCCN1]

To date, imidazoline compounds such as clonidine have not been appreciated as a local anesthetic for peripheral nerve blockade. Therefore, new compositions and methods are provided comprising an imidazoline compound for use as nerve blocks for the treatment of acute pain.

SUMMARY

Compositions and methods are provided comprising imidazoline compounds, such as clonidine or its pharmaceutically acceptable salts that are administered in order to treat acute pain by providing nerve blockade and local anesthesia to a target tissue site (e.g., bone, muscle, spine, etc.). The compositions and methods may, for example, be used to treat post-operative pain from surgical procedures and provide nerve blockade to the peripheral nerve fibers and/or peripheral nerve roots innervating the affected structure or region.

In some embodiments, there is an injectable pharmaceutical composition comprising a therapeutically effective amount of an imidazoline compound in a liquid pharmaceutical carrier, wherein the imidazoline compound provides local anesthesia and nerve block to the target tissue site which is a dorsal root ganglion, peripheral nerve fiber and/or peripheral nerve root. In some embodiments, the imidazoline compound is clonidine.

In some embodiments, there is an implantable medical device for reducing or treating acute pain in a patient in need of such treatment, the implantable medical device comprises an imidazoline compound disposed in at least one biodegradable polymer, the imidazoline compound disposed in the implantable medical device in a therapeutically effective amount to provide local anesthesia to a target tissue site under the skin of the patient, wherein the implantable medical device is configured to release the imidazoline compound over a period of at least 24 hours. In some embodiments, the imidazoline compound is clonidine.

In some embodiments, there is a method for providing nerve block to a patient in need of such treatment, the method comprising: administering an injectable pharmaceutical composition beneath skin of the patient, the injectable pharmaceutical composition comprising a therapeutically effective amount clonidine, wherein the clonidine provides local anesthesia and nerve block to a target tissue site under the skin of the patient, and the injectable pharmaceutical composition is configured to release the clonidine over a period of at least 24 hours.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent reading the following description, appended claims and accompanying drawings described below.

Figure 1:
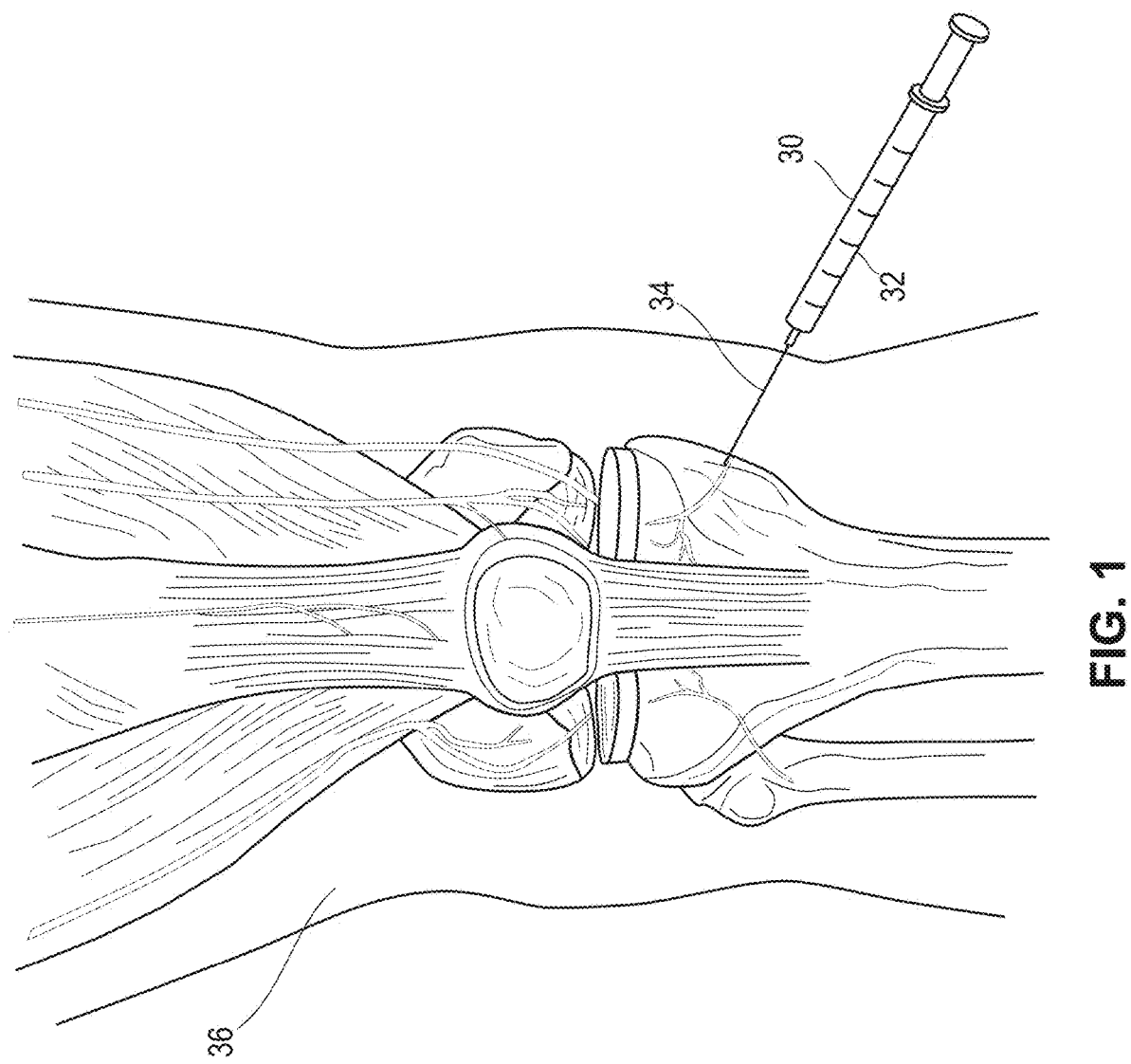
FIG. 1 illustrates an embodiment of an injectable pharmaceutical composition comprising a therapeutically effective amount of the imidazoline compound clonidine in a liquid pharmaceutical carrier. The injectable pharmaceutical composition is administered via a syringe under the epineurium of a medial genicular nerve to treat acute medial knee pain.

It is to be understood that the figure is not drawn to scale. Further, the relation between objects in a figure may not be to scale, and may in fact have a reverse relationship as to size. The figures are intended to bring understanding and clarity to the structure of each object shown, and thus, some features may be exaggerated to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Definitions

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

A "drug depot" is the composition in which the clonidine is administered to the body. Thus, a drug depot may comprise a physical structure (e.g., device) to facilitate implantation and retention in a desired site (e.g., a nerve, disc space, a spinal canal, a tissue of the patient, particularly at or near a site of post-operative pain, etc.). The drug depot (e.g., device) may also comprise the drug itself. The term "drug" as used herein is generally meant to refer to any substance that alters the physiology of a patient. The term "drug" may be used interchangeably herein with the terms "therapeutic agent," "therapeutically effective amount," and "active pharmaceutical ingredient" or "API." It will be understood that unless otherwise specified, a "drug" formulation may include one or more than one therapeutic agent, wherein exemplary combinations of therapeutic agents can include a combination of two or more drugs. The drug provides a concentration gradient of the therapeutic agent for delivery to the site. In various embodiments, the drug depot (e.g., device) provides an optimal drug concentration gradient of the therapeutic agent at a distance of up to about 0.01 cm to about 20 cm from the administration site and comprises clonidine. A "therapeutically effective amount" or "effective amount" is such that when administered, the drug results in alteration of the biological activity, such as, for example, inhibition or alleviation of pain by providing nerve block or local anesthesia. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments, the medical device or formulation is designed for immediate release. In other embodiments, the medical device or formulation is designed for sustained release. In other embodiments, the medical device or formulation comprises one or more immediate release surfaces and one or more sustained release surfaces.

A "depot" includes but is not limited to capsules, carriers, microspheres, microparticles, microcapsules, micro-depot particles, nanospheres, nanoparticles, coating, matrices, wafers, pills, pellets, emulsions, liposomes, beads, micelles, gels, suspensions, strips, ribbons, fibers or other pharmaceutical delivery compositions or a combination thereof. In some embodiments, a depot is a super-saturated injectable suspension.

Suitable materials for the depot (e.g., device) are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof.

Depots may include liposomes, silk, nylon, linen, cotton, chromic gut, plain gut, cat gut, vicryl, polyglactin, polyester, polypropylene, stainless steel, synthetic polymers having lactic acid or glycolic acid ester linkages subject to hydrolytic degradation to non-toxic tissue compatible absorbable components, including polylactic acid or polyglycolic acid, cholesterol, 1,2-dipalmitoyl-sn-glycero-3 phospho-rac-(1-glycerol) (DPPG), tricaprylin, 1, 2-dierucoylphosphatidylcholine (DEPC), or combinations thereof. The depot may be absorbable.

The term "biodegradable" includes that all or parts of the drug depot (e.g., device) will degrade over time by the action of enzymes, by hydrolytic action and/or by other similar mechanisms in the human body. In various embodiments, "biodegradable" includes that the depot (e.g., device) can break down or degrade within the body to non-toxic components after or while a therapeutic agent has been or is being released. By "bioerodible" it is meant that the depot will erode or degrade over time due, at least in part, to contact with substances found in the surrounding tissue, fluids or by cellular action. By "bioabsorbable" it is meant that the depot (e.g., device) will be broken down and absorbed within the human body, for example, by a cell or tissue. "Biocompatible" means that the depot (e.g., device) will not cause substantial tissue irritation or necrosis at the target tissue site.

In some embodiments, the drug depot (e.g., device) has pores that allow release of the drug from the depot (e.g., device). The drug depot (e.g., device) will allow fluid in the depot (e.g., device) to displace the drug. However, cell infiltration into the depot (e.g., device) will be prevented by the size of the pores of the depot (e.g., device). In this way, in some embodiments, the depot (e.g., device) should not function as a tissue scaffold and allow tissue growth. Rather, the drug depot (e.g., device) will solely be utilized for drug delivery. In some embodiments, the pores in the drug depot (e.g., device) will be less than 250 to 500 microns. This pore size will prevent cells from infiltrating the drug depot (e.g., device) and laying down scaffolding cells. Thus, in this embodiment, the drug will elute from the drug depot (e.g., device) as fluid enters the drug depot (e.g., device), but cells will be prevented from entering. In some embodiments, where there are little or no pores, the drug will elute out from the drug depot (e.g., device) by the action of enzymes, by hydrolytic action and/or by other similar mechanisms in the human body.

The phrases "sustained release" and "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the drug depot, or a device or component thereof, or as the result of metabolic transformation or dissolution of the therapeutic agent(s) or conjugates of therapeutic agent(s).

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug.

The two types of formulations (sustained release and immediate release) may be used in conjunction. The sustained release and immediate release may be in one or more of the same depots. In various embodiments, the sustained release and immediate release may be part of separate depots. For example, a bolus or immediate release formulation of clonidine may be placed at or near the target site and a sustained release formulation may also be placed at or near the same site. Thus, even after the bolus becomes completely accessible, the sustained release formulation would continue to provide the active ingredient for the intended tissue.

In various embodiments, the depot can be designed to cause an initial burst dose of therapeutic agent within the first 24 hours to 48 hours after implantation. "Initial burst" or "burst effect" "burst release" or "bolus dose" refers to the release of therapeutic agent from the depot (e.g., device) during the first 24 hours to 48 hours after the depot (e.g., device) comes in contact with an aqueous fluid (e.g., interstitial fluid, synovial fluid, cerebral spinal fluid, etc.). The "burst effect" is believed to be due to the increased release of therapeutic agent from the depot. In some embodiments, the depot has one or more burst release surfaces that releases about 10%, 15%, 20%, 25%, 30%, 35%, 45%, to about 50% of the drug over 24 or 48 hours.

"Treating" or "treatment" of a disease or condition refers to executing a protocol that may include administering one or more drugs to a patient (human, normal or otherwise, or other mammal), in an effort to alleviate signs or symptoms of the pain or condition. Alleviation can occur prior to signs or symptoms of the pain or condition appearing, as well as after their appearance. Thus, treating or treatment includes preventing or prevention of pain or an undesirable condition. In addition, treating or treatment does not require complete alleviation of signs or symptoms, does not require a cure, and specifically includes protocols that have only a marginal effect on the patient. "Reducing pain" includes a decrease in pain and does not require complete alleviation of pain signs or symptoms, and does not require a cure. In various embodiments, reducing pain includes even a marginal decrease in pain. By way of example, the administration of the effective dosage of clonidine may be used to prevent, treat or relieve the symptoms of pain and provide local anesthesia or nerve block for different surgical procedures or conditions. These surgical procedures/conditions may comprise post-operative pain and/or acute pain relief.

The term "implantable" as utilized herein refers to a biocompatible depot (e.g., implantable medical device) retaining potential for successful placement within a mammal. The expression "implantable depot", "implantable medical device" and expressions of the like import as utilized herein refers to an object implantable through surgery, injection, or other suitable means whose primary function is achieved either through its physical presence or mechanical properties.

The term "parenteral" as used herein refers to modes of administration that bypass the gastrointestinal tract, and include for example, intravenous, intramuscular, continuous or intermittent infusion, intraperitoneal, intrasternal, subcutaneous, intra-operatively, intrathecally, intradiscally, peridiscally, epidurally, perispinally, intraarticular injection or combinations thereof. In some embodiments, the injection is intrathecal, which refers to an injection into the spinal canal (intrathecal space surrounding the spinal cord). An injection may also be into a muscle or other tissue.

"Localized" delivery includes delivery where one or more drugs are deposited within a tissue, for example, a nerve root of the nervous system or a region of the brain, or in close proximity (within about 0.1 cm, or within about 10 cm, for example) thereto. For example, the drug dose delivered locally from the depot may be, for example, 10%, 20%, 30%, 40%, 50%, 60%, 70%, 80%, 90%, 95%, 99%, or 99.9% less than the oral dosage or injectable dose. In turn, systemic side effects, such as for example, liver transaminase elevations, hepatitis, liver failure, myopathy, constipation, etc. may be reduced or eliminated.

"Local anesthetic" refers to a drug that reduces or prevents sensation along the nerve. The local anesthetic will create a numbness and/or lack of pain transmission along the nerve. The local anesthetic can interrupt an axon or bundle of axons from propagating a signal beyond the point of treatment.

The term "mammal" refers to organisms from the taxonomy class "mammalian," including but not limited to humans, other primates such as chimpanzees, apes, orangutans and monkeys, rats, mice, cats, dogs, cows, horses, etc.

The phrase "pain management medication" includes one or more therapeutic agents that are administered to prevent, alleviate or remove pain entirely. These include anti-inflammatory agents, muscle relaxants, analgesics, anesthetics, narcotics, and so forth, and combinations thereof.

The phrase "release rate profile" refers to the percentage of active ingredient that is released over fixed units of time, e.g., mcg/hr, mcg/day, 10% per day, etc. As persons of ordinary skill in the art know, a release rate profile may, but need not be linear. By way of a non-limiting example, the depot may be a gel that releases the clonidine over a period of 24 to 48 hours.

The term "solid" is intended to mean a rigid material, while, "semi-solid" is intended to mean a material that has some degree of flexibility, thereby allowing the depot (e.g., device) to bend and conform to the surrounding tissue requirements.

"Targeted delivery system" provides delivery of one or more drugs depots (e.g., devices) at or near the target site as needed for treatment of pain, or to provide local anesthesia or nerve block.

In various embodiments, pain results from "post-surgical pain" or "post-operative pain" or "surgery-induced pain", which are used herein interchangeably, and refer to pain arising in the recovery period of seconds, minutes, hours, days or weeks following a surgical procedure (e.g., hernia repair, orthopedic or spine surgery, etc.). Surgical procedures include any procedure that penetrates beneath the skin and causes pain and/or inflammation to the patient. Surgical procedure also includes arthroscopic surgery, an excision of a mass, spinal fusion, thoracic, cervical, or lumbar surgery, pelvic surgery or a combination thereof.

The term "pain management medication" includes one or more therapeutic agents that are administered to reduce, prevent, alleviate or remove pain entirely. These include anti-inflammatory agents, muscle relaxants, analgesics, anesthetics, narcotics, etc., or combinations thereof.

In various embodiments, the post-surgical pain or post-operative pain or surgery-induced pain, is accompanied by inflammation. In some embodiments, the post-surgical pain, post-operative pain, or surgery-induced pain is not accompanied by inflammation. Inflammation can be an acute response to trauma or surgery. When tissues are damaged, TNF-α attaches to cells to cause them to release other cytokines that cause inflammation. The purpose of the inflammatory cascade is to promote healing of the damaged tissue, but once the tissue is healed, the inflammatory process does not necessarily end. Left unchecked, this can lead to degradation of surrounding tissues and associated pain. Thus, pain can become a disease state in itself. That is, when this pathway is activated, inflammation and pain ensue. Often a vicious and seemingly endless cycle of insult, inflammation, and pain sets in.

The abbreviation "DLG" refers to poly(DL-lactide-co-glycolide).

The abbreviation "DL" refers to poly(DL-lactide).

The abbreviation "LG" refers to poly(L-lactide-co-glycolide).

The abbreviation "CL" refers to polycaprolactone.

The abbreviation "DLCL" refers to poly(DL-lactide-co-caprolactone).

The abbreviation "LCL" refers to poly(L-lactide-co-caprolactone).

The abbreviation "G" refers to polyglycolide.

The abbreviation "PEG" refers to poly(ethylene glycol).

The abbreviation "PLGA" refers to poly(lactide-co-glycolide) also known as poly(lactic-co-glycolic acid), which are used interchangeably.

The abbreviation "PLA" refers to polylactide.

The abbreviation "PEA" refers to poly(ester) amides.

The abbreviation "POE" refers to poly(orthoester). The above polymers or combination of polymers can be in the drug depot (e.g., device).

Reference will now be made in detail to certain embodiments of the invention, examples of which are illustrated in the accompanying drawing. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

It will be understood that the section headings below are for convenience for the reader and one section heading can be combined with other section headings.

Imidazoline Compounds

Compositions comprising an imidazoline compound are provided. Imidazoline compounds include imidazoline derivatives thereof. In some embodiments, the composition comprises, consists of or consists essentially of the imidazoline compound. In some embodiments, the composition provides local anesthesia and nerve block to a target tissue site which can be for example, a dorsal root ganglion, peripheral nerve fiber and/or peripheral nerve root. The composition can also be administered to treat sciatica in a patient.

In some embodiments, the imidazoline compounds and/or alpha-2-adrenergic agonists, can include, for example, clonidine, p-aminoclonidine, tiamenidine, 5-bromo-6-(2 imidazolidine-2-ylamino) quinoxaline, dexmedetomidine, detomidine, medetomidine, oxymetazonline, brimonidine, tizanidine, mivazerol (UCB-Pharma, Belgium), lofexidine, xylazine, guanabenz, guanfacine, guanclofine, guanoxabenz, or a derivative or structural analogue thereof, alpha-methylnorepherine, azepexole, indoramin, 6-allyl-2-amino-5,6,7,8-tetrahydro-4H-thiazolo [4, 5-d] azepine diHCL and analogs thereof, guanethidine, methyldopa, xylometazoline, fadolmidine and combinations thereof.

Imidazoline compounds include hydrates and solvates. The term "solvate" as used herein refers to an aggregate or complex that comprises one or more molecules of a compound of the disclosure with one or more molecules of solvent. Examples of solvents that form solvates include, but are not limited to, water, isopropanol, ethanol, methanol, DMSO, ethyl acetate, acetic acid, and ethanolamine. The term "hydrate" refers to the aggregate or complex where the solvent molecule is water. The solvent may be inorganic solvents such as for example water in which case the solvate may be a hydrate. Alternatively, the solvent may be an organic solvent, such as ethanol. Thus, the compounds of the present disclosure may exist as a hydrate, including a monohydrate, dihydrate, hemihydrate, sesquihydrate, trihydrate, tetrahydrate or the like, as well as the corresponding solvated forms. The compound of the disclosure may be true solvates, while in other cases, the compound of the disclosure may merely retain adventitious water or be a mixture of water plus some adventitious solvent. When referring to the imidazoline compound, unless otherwise specified or apparent from context, it is to be understood that the inventors are also referring to pharmaceutically acceptable salts. Examples of potentially pharmaceutically acceptable salts include those salt-forming acids and bases that do not substantially increase the toxicity of a compound, such as, salts of alkali metals such as magnesium, potassium and ammonium, salts of mineral acids such as hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, and the like. One well-known commercially available salt for the imidazoline compound clonidine is its hydrochloride salt.

As described above, one particular imidazoline compound is clonidine. Further, when referring to the imidazoline compound or particularly clonidine, the active ingredient may not only be in the salt form, but also in the base form (e.g., free base). In various embodiments, if it is in the base form, it may be combined with polymers under conditions in which there is not severe polymer degradation, as may be seen upon heat or solvent processing that may occur with PLGA or PLA. By way of a non-limiting example, when formulating the imidazoline compound, such as clonidine with poly(orthoesters) it may be desirable to use the clonidine base formulation. By contrast, when formulating clonidine with PLGA, it may be desirable to use the HCl salt form. In some embodiments, the imidazoline compound, such as clonidine, may be incorporated into a polymer core with a polymer and then coated with the same or different polymer.

Pharmaceutically acceptable salts of imidazoline compound (e.g., clonidine) include salts prepared from pharmaceutically acceptable non-toxic bases or acids including inorganic or organic bases, inorganic or organic acids and fatty acids. Salts derived from inorganic bases include aluminum, ammonium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethyl amine, tripropylamine, tromethamine, and the like. When the compound of the current application is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Fatty acid salts may also be used, e.g., fatty acid salts having greater than 2 carbons, greater than 8 carbons or greater than 16 carbons, such as butyric, caprioc, caprylic, capric, lauric, mystiric, palmitic, stearic, arachidic or the like.

In some embodiments, in order to reduce the solubility of the imidazoline compound (e.g., clonidine) to assist in obtaining a controlled release depot (e.g., device such as an injectable suspension) effect, the imidazoline compound (e.g., clonidine) is utilized as the free base or utilized in a salt which has relatively lower solubility. For example, the present application can utilize an insoluble salt such as a fatty acid salt. Representative fatty acid salts include salts of oleic acid or linoleic acid. In some embodiments, fatty acid salts with between 8 to 20 carbons may be used to produce salts with low solubility, such as clonidine palmeate and clonidine stearate. In some embodiments, fatty acid salts with between 12 to 18 carbons are used. Other embodiments can utilize a lipid soluble salt of clonidine.

In some embodiments, the imidazoline compound (e.g., clonidine) is released locally from the depot at a dose in an amount between about 50 μg and 10,000 μg per day for a period of 24 to 48 hours after implantation at the target tissue site. In some embodiments, the initial burst or bolus release is about 2 to 20 times higher from 1 hour to about 48 hours than the sustained release daily dose released from the depot.

In some embodiments, the depot comprises an imidazoline compound (e.g., clonidine) that is in the depot in an amount of from about 3% to about 90% by weight. In some embodiments, the imidazoline compound (e.g., clonidine) is in the depot in an amount from about 5% to about 80% by weight. In some embodiments, the imidazoline compound (e.g., clonidine) is in the depot in an amount from about 10% to about 75% by weight. In some embodiments, the imidazoline compound (e.g., clonidine) is in the depot in an amount from about 75% to about 99.1% by weight. In some embodiments, the imidazoline compound (e.g., clonidine) is in the depot in an amount of about 5% by weight, or is in an amount of about 15% by weight.

In some embodiments, the imidazoline compound (e.g., clonidine) can be in powdered form having particle sizes predominantly in a range from about 1 to about 10 microns that can be reconstituted with the polymer for delivery. In some embodiments, the imidazoline compound (e.g., clonidine) can have a particle size from about 1 to about 20 microns. In various embodiments, the drug particle size of the imidazoline compound (e.g., clonidine compound) is from about 1 to 30 microns, however, in various embodiments, ranges from about 1 micron to 250 microns may be used.

In some embodiments, the implantable medical device comprises clonidine hydrochloride in an amount from about 3 wt. % to about 5 wt. % of the implantable medical device, poly(L-lactide-co-caprolactone comprising from about 85 wt. % to about 95 wt. % of the implantable medical device, and mannitol in an amount from about 2.5 wt. % to about 10 wt. % of the implantable medical device. The implantable medical device is configured to release the clonidine hydrochloride over a period of at least 1 to about 5 days.

In some embodiments, at least 75% of the particles have a size from about 1 micrometers to about 20 micrometers. In some embodiments, at least 85% of the particles have a size from about 1 micrometers to about 20 micrometers. In some embodiments, at least 95% of the particles have a size from about 1 micrometers to about 20 micrometers. In some embodiments, all of the particles have a size from about 1 micrometers to about 20 micrometers.

In some embodiments, at least 75% of the particles have a size from about 1 micrometers to about 100 micrometers. In some embodiments, at least 85% of the particles have a size from about 1 micrometers to about 100 micrometers. In some embodiments, at least 95% of the particles have a size from about 1 micrometers to about 100 micrometers. In some embodiments, all of the particles have a size from about 1 micrometers to about 100 micrometers.

In some embodiments, there is a pharmaceutical formulation comprising clonidine, wherein the clonidine is in a mixture of clonidine hydrochloride and clonidine base and the mixture comprises from about 3 wt. % to about 30 wt. % of the formulation and a biodegradable polymer comprises at least 70% of the formulation. In some embodiments, the polymer in this formulation is poly(L-lactide-co-caprolactone). In some embodiments, a pharmaceutical formulation is provided comprising 15 wt % clonidine or 15 wt % clonidine HCL and 85 wt % poly(D,L-lactide). In some embodiments, a pharmaceutical formulation is provided comprising 5 wt % clonidine or 5 wt % clonidine HCL and 95 wt % poly(D,L-lactide).

In some embodiments, the imidazoline compound can be administered as a monotherapy to provide nerve block and/or local anesthesia to a target tissue site, such as a dorsal root ganglion, peripheral nerve fiber and/or peripheral nerve root. Thus, the imidazoline is used as single therapy without the need for other local anesthetics and/or nerve blocking agents (e.g., lidocaine, bupivacaine, etc.). The imidazoline compound can also be administered to treat sciatica in a patient. In some embodiments, clonidine can be administered as the single imidazoline as monotherapy to provide nerve block and/or local anesthesia to a target tissue site, such as a dorsal root ganglion, peripheral nerve fiber and/or peripheral nerve root. This eliminates or reduces the need for other local anesthetics and/or nerve blocking agents (e.g., lidocaine, bupivacaine, etc.).

Excipients and Therapeutic Agents

The depot (e.g., device such as pellets, strips, fibers, injectable suspension etc.) may comprise other therapeutic agents in addition to the imidazoline compound (e.g., clonidine compound). These therapeutic agents, in various embodiments, block the transcription or translation of TNF-α or other proteins in the inflammation cascade. Suitable therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents include IL-1 inhibitors, such Kineret® (anakinra) which is a recombinant, nonglycosylated form of the human inerleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogs (which reduce TNF-α production by macrophages), bone morphogenetic protein (BMP) type 2 and BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that, where desirable, a pegylated form of the above may be used. Examples of still other therapeutic agents include NF kappa B inhibitors such as glucocorticoids, antioxidants, such as dithiocarbamate, and other compounds, such as, for example, sulfasalazine.

Examples of therapeutic agents suitable for use also include, but are not limited to an anti-inflammatory agent, an analgesic agent, or a combination thereof. Anti-inflammatory agents include, but are not limited to, apazone, celecoxib, diclofenac, diflunisal, enolic acids (piroxicam, meloxicam), etodolac, fenamates (mefenamic acid, meclofenamic acid), gold, ibuprofen, indomethacin, ketoprofen, ketorolac, nabumetone, naproxen, nimesulide, salicylates, sulfasalazine [2-hydroxy-5-[-4-[C2-pyridinylamino)sulfonyl]azo]benzoic acid, sulindac, tepoxalin or tolmetin; as well as antioxidants, such as dithiocarbamate; steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable anabolic growth or anti-catabolic growth factors include, but are not limited to, a bone morphogenetic protein, a LIM mineralization protein, CDMP or progenitor cells or a combination thereof.

Suitable analgesic agents include, but are not limited to, acetaminophen, bupivacaine, lidocaine, and opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine, amitriptyline, carbamazepine, gabapentin, pregabalin, or a combination thereof.

The therapeutic agent in the depot may include, but is not limited to, members of the fibroblast growth factor family, including acidic and basic fibroblast growth factor (FGF-1 and FGF-2) and FGF-4; members of the platelet-derived growth factor (PDGF) family, including PDGF-AB, PDGF-BB and PDGF-AA; EGFs; the TGF-β superfamily, including TGF-β1, 2 or 3; osteoid-inducing factor (OIF); angiogenin(s); endothelins; hepatocyte growth factor or keratinocyte growth factor; members of the bone morphogenetic proteins (BMPs) BMP-1, BMP-3, BMP-2; OP-1, BMP-2A, BMP-2B, or BMP-7; HBGF-1 or HBGF-2; growth differentiation factors (GDFs); members of the hedgehog family of proteins, including indian, sonic and desert hedgehog; ADMP-1; other members of the interleukin (IL) family; members of the colony-stimulating factor (CSF) family, including CSF-1, G-CSF, and GM-CSF, or isoforms thereof; VEGF, NELL-1 (neural epidermal growth factor-like 1), CD-RAP (cartilage-derived retinoic acid-sensitive protein) or combinations thereof.

The imidazoline compound (e.g., clonidine) may also be administered with non-active ingredients. These non-active ingredients may have multi-functional purposes including the carrying, stabilizing and controlling the release of the therapeutic agent(s). The sustained release process, for example, may be by a solution-diffusion mechanism or it may be governed by an erosion-sustained process. Typically, the depot (e.g., device) will be a solid or semi-solid formulation comprised of a biocompatible material that can be biodegradable.

Excipients, plasticizers, and/or pore forming agents may be formulated with the imidazoline compound (e.g., clonidine) in addition to the biodegradable polymer. Plasticizers and/or pore forming agents impart malleability to the resulting formulations. Additionally, plasticizers and/or pore forming agents make the biodegradable polymer more porous after implantation, creating a controlled burst release of the clonidine. In some embodiments, the plasticizers and/or pore forming agents include but are not limited to MgO (e.g., 1 wt. %), mPEG, propylene glycol, mannitol, trehalose, TBO-Ac, Span-65, Span-85, pluronic F127, sorbitol, xylitol, isomalt, erithritol, cyclodextrin, maltodextrin, pluronic F68, CaCl, dextran, dextran sulphate, dextran phosphate, hydroxypropylcellulose, ethylcellulose, PEG 1500, PEG 400, PEG3350, acetyl tributyl citrate, butyl benzyl phthalate, butyl phthalyl butyl glycolate, dibutyl phthalate, dibutyl sebacate, diethyl phthalate, diethylene glycol dibenzoate, dipropylene glycol, dipropylene glycol dibenzoate, ethyl phthalyl ethyl glycolate, ethyl-p-toluene sulfonamide, hexylene glycol, methyl phthalyl ethyl glycolate, polyoxyethylene aryl ether and tributoxyethyl phthalate or combinations thereof. Other plasticizers that may be utilized include esters of ortho, iso and terephthalate, esters of citric acid, esters of 1,2-, 1,3- and 1,4-cyclohexane dicarboxylic acid, and anhydrides or combinations thereof. Diluent plasticizers such as 2-ethylhexyl benzoate, isodecyl benzoate or 2,2,4-trimethyl-1,3-pentanediol diisobutyrate may also be used to control rheology and other properties. Diluents which may be utilized include aromatic hydrocarbon, cycloaliphatic hydrocarbon, and aliphatic hydrocarbons. In some embodiments, the particle size of the plasticizer and/or excipient (e.g., mannitol) is about 1 to about 250 microns, about 1 to about 100 microns or about 1 to about 10 microns. In various embodiments, Dv 10 or Dv 50 is about 1 to about 100 microns. In some embodiments, the plasticizer and or pore forming agent is amorphous and/or crystalline. In various embodiments, mannitol is crystalline and not amorphous.

In some embodiments, the pore forming agent comprises from about 0.5 wt. % to about 50 wt. % of the formulation. In some embodiments, the pore forming agent comprises from about 1.0 wt. % to about 40 wt. % of the formulation. In some embodiments, the pore forming agent comprises from about 1 wt. % to about 30 wt. % of the formulation. In some embodiments, the pore forming agent comprises from about 5 wt. % to about 20 wt. % of the formulation. In some embodiments, the pore forming agent comprises from about 2 wt. % to about 10 wt. % of the formulation. In some embodiments, the pore forming agent comprises from about 2.5 wt. % to about 30 wt. % of the formulation. In some embodiments, the pore forming agent comprises from about 1 wt. % to about 3 wt. % of the formulation.

In particular embodiments, the pore forming agent or plasticizer comprises 1%, 1.5%, 2%, 2.5%, 3%, 3.5%, 4%, 4.5%, 5%, 5.5%, 6%, 6.5%, 7%, 7.5%, 8%, 8.5%, 9%, 9.5% to about 10% % w/w, w/v, or v/v of the composition.

In some embodiments, the other excipients comprise from about 0.001 wt. % to about 50 wt. % of the formulation. In some embodiments, the excipients comprise from about 0.001 wt. % to about 40 wt. % of the formulation. In some embodiments, the excipients comprise from about 1 wt. % to about 30 wt. % of the formulation. In some embodiments, the excipients comprise from about 5 wt. % to about 20 wt. % of the formulation. In some embodiments, the excipients comprise from about 2 wt. % to about 10 wt. % of the formulation. In some embodiments, the excipients comprise from about 2.5 wt. % to about 30 wt. % of the formulation. In some embodiments, the excipients comprise from about 1 wt. % to about 3 wt. % of the formulation.

The imidazoline compound (e.g., clonidine) or its pharmaceutically acceptable salt may be administered with a muscle relaxant. Exemplary muscle relaxants include by way of example and not limitation, alcuronium chloride, atracurium bescylate, carbamate, carbolonium, carisoprodol, chlorphenesin, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

Injectable

In some embodiments, the imidazoline compound (e.g., clonidine) is administered via a bolus infusion, a continuous infusion, an intravenous administration (I.V.), an intramuscular administration, an intrathecal administration, a subcutaneous administration, an epidural administration, a parenteral administration, an intra-articular administration, a direct application or deposition onto or adjacent to a target tissue site of the pathological condition, and any combinations thereof.

In some embodiments, the imidazoline compound (e.g., clonidine) is administered parenterally, for example, by injection. Parenteral refers to modes of administration that bypass the gastrointestinal tract, and include for example, intravenous, intramuscular, continuous or intermittent infusion, intraperitoneal, intrasternal, subcutaneous, intra-operatively, intrathecally, intradiscally, peridiscally, epidurally, perispinally, intraarticular injection or combinations thereof. In some embodiments, the injection is intrathecal, which refers to an injection into the spinal canal (intrathecal space surrounding the spinal cord). An injection may also be into a muscle or other tissue. In some embodiments, the imidazoline compound (e.g., clonidine) is administered continuously via a catheter or through I.V. administration.

In some embodiments, as shown in FIG. 1, the pharmaceutical composition or device comprising an imidazoline compound (e.g., clonidine) 30 can be injectable and is administered via a syringe 32 having a needle 34 to a target tissue site 36. In some embodiments, the pharmaceutical composition or device is administered to a surgical site that is under the epineurium of a medial genicular nerve for acute medial knee pain.

In some embodiments, the dosage of imidazoline compound (e.g., clonidine) injected locally at or near the target tissue site may be from approximately 50 μg and 10,000 μg per day or hour to provide nerve block and local anesthesia at or near the target tissue site, as described above. In some embodiments, the dosage of the imidazoline compound (e.g., clonidine) injected locally at or near the target tissue site may be from about 50, 75, 100, 125, 150, 175, 200, 250, 300, 350, 400, 500, 750, 1,000, 1,250, 1,500, 2,000 2,250, 5,000, 7,500 to about 10,000 μg per day or hour.

In some embodiments, the imidazoline compound (e.g., clonidine) is provided in a liquid pharmaceutical carrier for injectable administration. In some embodiments, the liquid pharmaceutical carrier includes, but is not limited to sodium chloride, dextrose, other sugars including but not limited to sucrose, fructose, glucose, lactated ringer's, polyols including but not limited to mannitol, xylitol, sorbitol, maltitol, lactitol, polysaccharides including but not limited to native or pre-gelatinized starch, maltodextrins, cyclodextrins, mineral compounds including but not limited to dicalcium or tricalcium phosphate, either dihydrate or anhydrous, cellulose derivatives including but not limited to microcrystalline cellulose, lactoses either monohydrates thereof or anhydrous, as well as their mixtures such as dicalcium phosphate dihydrate, mannitol, pre-gelatinized maize starch, microcrystalline cellulose and their mixtures, sterile water and/or NaCl (saline). In some embodiments, the saline is 0.90% saline or 0.45% saline. In some embodiments, the liquid pharmaceutical carrier is preservative free. In some embodiments, the imidazoline compound (e.g., clonidine) is administered in a single injection or multiple injections. In some embodiments, the imidazoline compound (e.g., clonidine) is administered in 1, 2, 3, 4, 5, 6, 7, 8, 9, 10, 11, 12, 13, 14, 15, 16, 17, 18, 19 or 20 injections.

In some embodiments, an injectable pharmaceutical composition is provided comprising particles of the imidazoline compound, from about 1 to about 10 microns in diameter, that are suspended in a non-polar carrier. Suitable non-polar carriers include, but are not limited to low viscosity oils, such as sesame seed oil, cottonseed oil, safflower oil, olive oil, corn oil, almond oil, peanut oil, poppy seed oil, soybean oil and/or castor oil. The non-polar carriers may be suitable for high gauge needles to treat small nerves and may further retard dissolution, rendering free imidazoline compound. In some embodiments, the imidazoline compound is clonidine. In some embodiments, the non-polar carrier can be in an amount of from about 20 to about 200 milli-Molar, from about 10 to about 100 milli-Molar or from about 1 to about 10 milli-Molar.

In some embodiments, an injectable pharmaceutical composition is provided comprising solid imidazoline compound particles disposed in an emulsion. The solid imidazoline compound particles are suspended in an oil phase and dissolved in a liquid phase for a burst release onset of action. In some embodiments, the liquid phase of the composition may contain up to 200 mcg of solid imidazoline compound such as clonidine, with base or salt particles comprising the remainder of about a 1 to about 2 mg total dose.

In some embodiments, the imidazoline compound (e.g., clonidine) is administered in a super saturated injectable suspension. The super saturated injectable suspension comprising the imidazoline compound (e.g., clonidine) can be administered to the target tissue site at a dose, such as, for example, from about 50 μg and 10,000 μg per day or hour.

In some embodiments, the clonidine has a particle size where at least 75% of the particles have a size from about 0.5 micrometer to about 100 micrometers. In some embodiments, at least 85% of the particles have a size from about 0.5 micrometers to about 100 micrometers. In some embodiments, at least 95% of the particles have a size from about 0.5 micrometer to about 100 micrometers. In some embodiments, all of the particles have a size from about 0.5 micrometer to about 100 micrometers. In some embodiments, at least 80% of the particles have a size from 2 microns to about 50 microns on a volume basis.

In some embodiments, the clonidine has a particle size where at least 75% of the particles have a size from about 1 nanometer to about 1000 nanometers. In some embodiments, at least 85% of the particles have a size from 1 nanometer to about 500 nanometers. In some embodiments, at least 95% of the particles have a size from about 50 nanometers to about 500 nanometers. In some embodiments, all of the particles have a size from about 100 nanometers to about 750 nanometers.

Drug Depot

In some embodiments, the implantable medical device comprises a drug depot (e.g., pellets, strips, fibers, injectable suspension etc.). In various embodiments, a plurality of drug depots can be administered to a surgical site. In some embodiments, a plurality of drug depots are provided (e.g., in a kit) and administered to a surgical site and triangulate and/or surround the site to treat post-operative pain. In various embodiments, a plurality of drug depots comprise about 1, 2, 3, 4, 5, 6, 7, 8, 9 or 10 drug depots.

In some embodiments, the drug depot has a melting point or glass transition temperature close to or higher than body temperature, but lower than the decomposition or degradation temperature of the therapeutic agent. However, the pre-determined erosion of the depot (e.g., device) material can also be used to provide for slow release of the loaded therapeutic agent(s). Non-biodegradable polymers include but are not limited to PVC and polyurethane. In some embodiments, a plasticizer is used to lower glass translation temperature in order to affect stability of the device.

In various embodiments, the depot comprises the imidazoline compound (e.g., clonidine) and a biodegradable polymer in amorphous, crystalline or semicrystalline form; where the crystalline form may include polymorphs, solvates or hydrates.

In some embodiments, the depot has a modulus of elasticity in the range of about $1 \times 10^2$ to about $6 \times 10^5$ dyn/cm$^2$, or $2 \times 10^4$ to about $5 \times 10^5$ dyn/cm$^2$, or $5 \times 10^4$ to about $5 \times 10^5$ dyn/cm$^2$. In some embodiments, the device is in the form of a solid.

In some embodiments, the imidazoline compound (e.g., clonidine) is administered in a device that is solid or in semi-solid form. The solid or semi-solid form of the device may have a pre-dosed viscosity in the range of about 1 to about 2000 centipoise (cps), 1 to about 200 cps, or 1 to about 100 cps. After the solid or semi-solid device is administered to the target site, the viscosity of the semi-solid or solid depot will increase and the semi-solid will have a modulus of elasticity in the range of about $1 \times 10^2$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

In various embodiments, the semi-solid or solid depot may comprise a polymer having a molecular weight (MW), as shown by the inherent viscosity (IV), from about 0.10 dL/g to about 1.2 dL/g or from about 0.20 dL/g to about 0.50 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.55 dL/g, about 0.50 to about 0.70 dL/g, about 0.55 to about 0.6 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 dL/g, about 1.1 to about 1.3 dL/g, about 1.2 to about 1.4 dL/g, about 1.3 to about 1.5 dL/g, about 1.4 to about 1.6 dL/g, about 1.5 to about 1.7 dL/g, about 1.6 to about 1.8 dL/g, about 1.7 to about 1.9 dL/g, or about 1.8 to about 2.1 dL/g.

In some embodiments, the depot may comprise an 8% loaded 60:40 LCL 5A with a 6.5% content having a 0.1 mm diameter; an 8% loaded 60:40 LCL 5A with a 6.6% content having a 0.1 mm diameter; or a 16% loaded 60:40 LCL 5A with a 13.2% content having a 0.1 mm diameter. In some embodiments, the depot comprises 15 wt % clonidine or 15 wt % clonidine HCL and 85 wt % poly(D,L-lactide), where the poly(D,L-lactide) has a molecular weight of from about 1,000 to about 10,000,000 Da. In some embodiments, the depot comprises 5 wt % clonidine or 5 wt % clonidine HCL and 95 wt % poly(D,L-lactide), where the poly(D,L-lactide) has a molecular weight of from about 1,000 to about 10,000,000 Da.

In some embodiments, the depot comprises 5 wt % clonidine HCL having an ester end group, and 95 wt % poly(D,L-lactide). The poly(D,L-lactide) has a molecular weight of about 70,000 Da and an I.V. of about 0.45-0.55 DL/g. The depot has a diameter of about 0.75 mm, and a length of about 4 mm so that the depot can be administered through an 18 gauge needle. The depot provides a burst release of the clonidine HCL of about 5-10% of the total amount of the clonidine HCL in a period of about 24 hours or 2-40 mcg in about 24 hours. In this embodiment, about 50% of the total cumulative dose of the clonidine HCL remains for 60 days or more. In this embodiment, about 80% of the clonidine HCL particles are from about 5 to about 150 microns or from about 5 to about 100 microns. The dosing is about 0.5 mcg/day up to about 5 mcg/day over a period of 24 hours, and then continues release for about 70 days.

In some embodiments, the depot comprises 8 wt % clonidine HCL having an ester end group, and 92 wt % poly(D,L-lactide). The poly(D,L-lactide) has a molecular weight of about 70,000 Da and an I.V. of about 0.45-0.55 DL/g. The depot has a diameter of about 0.75 mm, and a length of about 4 mm so that the depot can be administered through an 18 gauge needle. The depot provides a burst release of the clonidine hydrochloride of about 5-10% of the total amount of the clonidine hydrochloride in a period of about 24 hours or 5 to 6 mcg in about 24 hours. The depot then releases about 1 mcg/day up to 20 mcg/day via a sustained release for about 50 days, and then the release decreases to about 0.1 mcg to about 10 mcg/day for longer than 70 days. In this embodiment, about 50% of the total cumulative dose of the clonidine HCL releases between about 30 to about 42 days and about 80% of the clonidine HCL is released at about 70 days. In this embodiment, about 80% of the clonidine HCL particles are from about 5 to about 150 microns or about 5 to about 100 microns.

In some embodiments, the depot comprises 15 wt % clonidine HCL having an ester end group, and 85 wt % poly(D,L-lactide). The poly(D,L-lactide) has a molecular weight of about 70,000 Da and an I.V. of about 0.45-0.55 DL/g. The depot has a diameter of about 0.75 mm, and a length of about 4 mm so that the depot can be administered through an 18 gauge needle. The depot provides a burst release of about 5-10% of the total amount of the clonidine HCL in a period of about 24 hours or 20 mcg-150 mcg in about 24 hours. The clonidine HCL is then released in an amount of about 5 mcg/day up to about 80 mcg/day via sustained release for about 28 days or 30 days. Then at 28-50 days, the release of the clonidine HCL decreases to about 0.1 mcg to about 5 mcg/day for more than 70 days. In this embodiment, 80% of total cumulative dose of the clonidine HCL is released in 35 days and 20% of the clonidine HCL is released over several months. In this embodiment, about 80% of the clonidine HCL particles are from about 5 to about 150 microns or from about 5 to about 100 microns.

In some embodiments, the depot may not be fully biodegradable. For example, the device may comprise polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon device, glass device, plastics, ceramics, methacrylates, poly (N-isopropylacrylamide), PEO-PPO-PEO (pluronics) or combinations thereof.

In some instances, it may be desirable to avoid having to remove the depot after use. In those instances, the depot may comprise a biodegradable material. There are numerous materials available for this purpose and having the characteristic of being able to breakdown or disintegrate over a prolonged period of time when positioned at or near the target tissue. As a function of the chemistry of the biodegradable material, the mechanism of the degradation process can be hydrolytical or enzymatical in nature, or both. In various embodiments, the degradation can occur either at the surface (heterogeneous or surface erosion) or uniformly throughout the drug delivery system depot (e.g., device) (homogeneous or bulk erosion).

In various embodiments, the depot (e.g., device) may comprise a bioerodible, a bioabsorbable, and/or a biodegradable biopolymer that may provide immediate release, or sustained release of the clonidine. Examples of suitable sustained release biopolymers include but are not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), poly(orthoester)s (POE), poly(esteramide)s, polyaspirins, polyphosphagenes, starch, pre-gelatinized starch, hyaluronic acid, chitosans, gelatin, alginates, albumin, fibrin, vitamin E compounds, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof.

In some embodiments, the depot comprises biodegradable polymers, wherein the at least one biodegradable polymer comprises one or more of poly(lactide-co-glycolide) (PLGA), polylactide (PLA), polyglycolide (PGA), D-lactide, D,L-lactide, L-lactide, D,L-lactide-co-ε-caprolactone, L-lactide-co-ε-caprolactone, D,L-lactide-co-glycolide-co-ε-caprolactone, poly(D,L-lactide-co-caprolactone), poly(L-lactide-co-caprolactone), poly(D-lactide-co-caprolactone), poly(D,L-lactide), poly(D-lactide), poly(L-lactide), poly(esteramide) or a combination thereof.

In some embodiments, the drug depot comprises at least one biodegradable material in a wt % of about 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 65%, 60%, 55%, 50%, 40%, 45%, 35%, 25%, 20%, 15%, 10%, or 5% based on the total weight of the depot and the remainder is active and/or inactive pharmaceutical ingredients.

In some embodiments, the at least one biodegradable polymer comprises poly(L-lactide-co-caprolactone). In various embodiments, there is at least 95% poly(L-lactide-co-caprolactone); at least 90% poly(L-lactide-co-caprolactone); at least 85% poly(L-lactide-co-caprolactone); at least 80% poly(L-lactide-co-caprolactone); at least 75% poly(L-lactide-co-caprolactone); at least 70% poly(L-lactide-co-caprolactone); at least 65% poly(L-lactide-co-caprolactone); at least 60% poly(L-lactide-co-caprolactone); at least 55% poly(L-lactide-co-caprolactone); at least 50% poly(L-lactide-co-caprolactone); at least 45% poly(L-lactide-co-caprolactone); at least 40% poly(L-lactide-co-caprolactone); at least 35% poly(L-lactide-co-caprolactone); at least 30% poly(L-lactide-co-caprolactone); at least 25% poly(L-lactide-co-caprolactone); at least 20% poly(L-lactide-co-caprolactone); at least 15% poly(L-lactide-co-caprolactone); at least 10% poly(L-lactide-co-caprolactone); or at least 5% poly(L-lactide-co-caprolactone).

In some embodiments, at least 75% of the biodegradable polymer particles have a size from about 10 micrometers to about 200 micrometers. In some embodiments, at least 85% of the particles have a size from about 10 micrometers to about 200 micrometers. In some embodiments, at least 95% of the particles have a size from about 10 micrometers to about 200 micrometers. In some embodiments, all of the particles have a size from about 10 micrometers to about 200 micrometers.

In some embodiments, at least 75% of the biodegradable polymer particles have a size from about 20 micrometers to about 180 micrometers. In some embodiments, at least 85% of the particles have a size from about 20 micrometers to about 180 micrometers. In some embodiments, at least 95% of the particles have a size from about 20 micrometer to about 180 micrometers. In some embodiments, all of the particles have a size from about 20 micrometer to about 180 micrometers.

In some embodiments, there is a pharmaceutical formulation comprising the imidazoline compound clonidine, wherein the clonidine is in a mixture of clonidine hydrochloride and clonidine base and the mixture comprises from about 3 wt. % to about 30 wt. % of the formulation and a biodegradable polymer comprises at least 70% of the formulation. In some embodiments, the polymer in this formulation is poly(L-lactide-co-caprolactone).

In some embodiments, the polymer is poly(L-lactide-co-caprolactone) or poly(D,L-lactide-co-caprolactone). In some embodiments, poly(L-lactide-co-caprolactone) has better handling characteristics (flexibility, reduced friability, ease of delivery, etc.) than poly(D,L-lactide-co-caprolactone) and allows the depot to be delivered for acute pain (e.g., post-operative pain). In various embodiments, poly(L-lactide-co-caprolactone) is suitable for burst release and delivery of clonidine for post-operative pain. In some embodiments, the poly(D,L-lactide-co-caprolactone) does not have handling characteristics and a release profile suitable for treatment of pain (e.g., acute pain). For example, the burst release can be in some embodiments, about 5%, 10%, 15%, 20%, 25%, 30%, 35%, 45%, 50%, 55%, 60%, 65%, 70%, 75%, 80%, 85%, 90%, 95% to about 99% of the clonidine loaded in the depot over about 24 to 48 hours.

Mannitol, trehalose, dextran, mPEG and/or PEG may be used as a plasticizer or pore forming agent for the polymer as well as the plasticizers or pore forming agents described above. In some embodiments, the polymer and/or plasticizer may also be coated on the depot to provide the desired release profile. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the drug from the depot (e.g., device). In some embodiments, the range of the coating on the depot ranges from about 5 microns to about 250 microns or 5 microns to about 200 microns to delay release from the device.

In various embodiments, the depot comprises poly(lactide-co-glycolide) (PLGA), polylactide (PLA), polyglycolide (PGA), D-lactide, D,L-lactide, L-lactide, D,L-lactide-co-ε-caprolactone, L-lactide-co-ε-caprolactone, D,L-lactide-co-glycolide-co-ε-caprolactone, poly(D,L-lactide-co-caprolactone), poly(L-lactide-co-caprolactone), poly(D-lactide-co-caprolactone), poly(D,L-lactide), poly(D-lactide), poly(L-lactide), poly(esteramide), poly(L-lactide-co-ε-caprolactone), poly(D,L-lactide-co-ε-caprolactone) or a combination thereof and has an inherent viscosity of 0.2 to about 0.5 dL/g, or 0.4 to about 0.6 dL/g, or 0.6 to about 1.0 dL/gm and a MW of about 30,000 to about 125,000 Da.

In some embodiments, the depot comprises one or more polymers having a MW of from about 15,000 to about 150,000 Da, from about 25,000 to about 100,000 Da or from about 30,000 to about 50,000 Da or about 30,000 Da to about 60,000 Da.

In some embodiments, the depot comprises a polymer having an average molecular weight of the polymer can be from about 1,000 to about 10,000,000 Da; or about 1,000 to about 1,000,000 Da; or about 5,000 Da to about 500,000 Da; or about 10,000 Da to about 100,000 Da; or about 20,000 Da to 50,000 Da.

In some embodiments, when the polymer materials have different chemistries (e.g., high MW DLG 5050 and low MW DL), the high MW polymer may degrade faster than the low MW polymer.

As persons of ordinary skill in the art are aware, an implantable depot (e.g., device) compositions having a blend of polymers with different end groups are used the resulting formulation will have a lower burst index and a regulated duration of delivery. For example, one may use polymers with acid (e.g., carboxylic acid) and ester end groups (e.g., methyl or ethyl ester end groups).

Additionally, by varying the comonomer ratio of the various monomers that form a polymer (e.g., the L/G (lactic acid/glycolic acid) or G/CL (glycolic acid/polycaprolactone) ratio for a given polymer) there will be a resulting depot (e.g., device) composition having a regulated burst index and duration of delivery. For example, a depot (e.g., device) composition having a polymer with a L/G ratio of 50:50 may have a short duration of delivery ranging from about two days to about five days; a depot (e.g., device) composition having a polymer with a L/G ratio of 65:35 may have a duration of delivery of about two months; a depot (e.g., device) composition having a polymer with a L/G ratio of 75:25 or L/CL ratio of 75:25 may have a duration of delivery of about three months to about four months; a depot (e.g., device) composition having a polymer ratio with a L/G ratio of 85:15 may have a duration of delivery of about five months; a depot (e.g., device) composition having a polymer with a L/CL ratio of 25:75 or PLA may have a duration of delivery greater than or equal to six months; a depot (e.g., device) composition having a terpolymer of CL/G/L with G greater than 50% and L greater than 10% may have a duration of delivery of about one month and a depot (e.g., device) composition having a terpolymer of CL/G/L with G less than 50% and L less than 10% may have a duration months up to six months. In general, increasing the G content relative to the CL content shortens the duration of delivery whereas increasing the CL content relative to the G content lengthens the duration of delivery. Thus, among other things, depot (e.g., device) compositions having a blend of polymers having different molecular weights, end groups and comonomer ratios can be used to create a depot (e.g., device) formulation having a lower initial burst and a regulated duration of delivery.

The depot (e.g., device) may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfite, sodium thiosulfate, thimerosal, methylparaben, polyvinyl alcohol and phenylethyl alcohol; solubility adjusting agents; stabilizers; and/or cohesion modifiers. If the depot (e.g., device) is to be placed in the spinal area, in various embodiments, the depot (e.g., device) may comprise sterile preservative free material.

The depot (e.g., device) can be different sizes, shapes and configurations. There are several factors that can be taken into consideration in determining the size, shape and configuration of the depot. For example, both the size and shape may allow for ease in positioning the depot at the target tissue site that is selected as the implantation. In addition, the shape and size of the system should be selected so as to minimize or prevent the depot from moving after implantation. In various embodiments, the depot can be shaped like a rod or a flat surface such as a film or sheet (e.g., ribbon-like) or the like. Flexibility may be a consideration so as to facilitate placement of the device.

In various embodiments, the depot can be different sizes, for example, the device may be a length of from about 0.01 mm to 50 mm and have a diameter of from about 0.01 to about 4 mm. In various embodiments, as the diameter decreases, the surface area that comes in contact with the bodily fluid of the depot (e.g., device) increases and therefore release of the drug from the depot (e.g., device) increases. In various embodiments, the device may have a layer thickness of from about 0.005 to 1.0 mm, such as, for example, from 0.05 to 0.75 mm. In various embodiments, the length of the device is determined based on the length needed to treat the target tissue site.

Radiographic markers can be included on the device to permit the user to position the depot (e.g., device) accurately into the target site of the patient. These radiographic markers will also permit the user to track movement and degradation of the depot (e.g., device) at the site over time. In this embodiment, the user may accurately position the depot (e.g., device) in the site using any of the numerous diagnostic imaging procedures. Such diagnostic imaging procedures include, for example, X-ray imaging or fluoroscopy. Examples of such radiographic markers include, but are not limited to, barium, phosphate, bismuth, iodine, tantalum, tungsten, and/or metal beads or particles. In various embodiments, the radiographic marker could be a spherical shape or a ring around the depot (e.g., device).

In some embodiments, a drug depot is provided that controls delivery of therapeutic agents to local, target tissues and secures itself to a target tissue site. In some embodiments, the drug depot is a flexible, drug loaded device that attaches to a target tissue site, such as, for example, muscle and/or fascia. In various embodiments, the device attaches to the target tissue site via adhesives that are applied to the entire device or at the ends of the device. In some embodiments, the drug depot is flexible, biodegradable devices or strands that are drug loaded and/or drug coated to provide sustained release of a therapeutic to a local tissue site. In some embodiments, drug release is in days to months. In some embodiments, the drug depot comprises polymers, such as, for example, 5:95 poly(D,L-lactide-co-caprolactone), 10:90 poly(D,L-lactide-co-caprolactone), 15:85 poly(D,L-lactide-co-caprolactone), 20:80 poly(D,L-lactide-cocaprolactone), 25:75 poly(D,L-lactide-co-caprolactone), 30:70 poly(D,L-lactide-co-caprolactone), 35:65 poly(D,L-lactide-co-caprolactone), 40:60 poly(D,L-lactide-co-caprolactone), 45:55 poly(D,L-lactide-co-caprolactone), 50:50 poly(D,L-lactide-co-caprolactone), 55:45 poly(D,L-lactide-co-caprolactone), 60:40 poly(D,L-lactide-co-caprolactone), 65:35 poly(D,L-lactide-co-caprolactone), 70:30 poly(D,L-lactide-co-caprolactone), 75:25 poly(D,L-lactide-co-caprolactone), 80:20 poly(D,L-lactide-co-caprolactone), 85:15 poly(D,L-lactide-co-caprolactone), 90:10 poly(D,L-lactide-co-caprolactone) or 95:5 poly(D,L-lactide-co-caprolactone).

Degradation times for the polymers could be one day to 7 days. In some embodiments, the degradation time is about 1 day to about 5 days. In some embodiments, the degradation time is about 1 day, 2 days, 3 days, 4 days, 5 days, 6 days, to about 7 days.

In some embodiments, the imidazoline compound (e.g., clonidine) is coated on the device or uniformly distributed throughout the device. In various embodiments, the device is memory shape device and can comprise shape memory polymers including various polyethers, polyacrylates, polyamides, polysiloxanes, polyurethanes, polyether amides, polyurethane/ureas, polyether esters, or urethanelbutadiene copolymers or a combination thereof.

In some embodiments, the device provides a scaffold to release clonidine in vivo in three dimensions. In some embodiments, one or more devices may be stacked on one another.

In some embodiments, the device comprises a plurality of pores. In some embodiments, at least 10% of the pores are between about 10 micrometers and about 500 micrometers at their widest points. In some embodiments, at least 20% of the pores are between about 50 micrometers and about 150 micrometers at their widest points. In some embodiments, at least 30% of the pores are between about 30 micrometers and about 70 micrometers at their widest points. In some embodiments, at least 50% of the pores are between about 10 micrometers and about 500 micrometers at their widest points. In some embodiments, at least 90% of the pores are between about 50 micrometers and about 150 micrometers at their widest points. In some embodiments, at least 95% of the pores are between about 100 micrometers and about 250 micrometers at their widest points. In some embodiments, 100% of the pores are between about 10 micrometers and about 300 micrometers at their widest points.

In some embodiments, the device has a porosity of at least about 30%, at least about 50%, at least about 60%, at least about 70%, at least about 90%. The pore enhances release of the clonidine and supports pain relief to a patient after a surgical procedure.

In some embodiments, the initial burst surfaces can be disposed on the edges of the device so that upon contact with the target tissue site, the edges will begin to release the clonidine. In some embodiments, the body of the depot can comprise dense, entangled polymers and have the clonidine to provide slower release of the clonidine.

Alternatively, the imidazoline compound (e.g., clonidine) can be disposed homogenously throughout the depot to provide continuous extended release of the imidazoline compound (e.g., clonidine). In some embodiments, the imidazoline compound (e.g., clonidine) can be layered in the depot with some portions having different concentrations to provide burst release and then slower release of the clonidine in areas that have dense crosslinked polymers, such as for example, in the core of the device.

In some embodiments, the drug depot may have a burst release surface that releases about 5%, 10%, 15%, 20%, 25%, 30%, 35%, 45%, 50%, 55%, 60%, 65%, 70%, 75%, 80%, 85%, 90%, 95% to about 99% of the imidazoline compound (e.g., clonidine) over about 24 to 48 hours.

In various embodiments, 1 to about 10 drug depots (e.g., pellets, strips, fibers, etc.) having an initial burst dose of about 5 to about 15% may be provided to a surgical site. In some embodiments, 1 drug depot may comprise an initial burst of about 5 to about 15% within 4 hours and about 10% to about 25% cumulative release in 24 hours to provide pain relief.

In some embodiments, the device may comprise natural and/or synthetic material. For example, the device may comprise poly (alpha-hydroxy acids), poly (lactide-co-glycolide) (PLGA), polylactide (PLA), polyglycolide (PG), polyethylene glycol (PEG) conjugates of poly (alpha-hydroxy acids), polyorthoesters (POE), polyaspirins, polyphosphagenes, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, polyglycolide (PGA), D-lactide, D,L-lactide, L-lactide, D,L-lactide-co-ε-caprolactone, L-lactide-co-ε-caprolactone, D,L-lactide-co-glycolide-co-ε-caprolactone, poly(D,L-lactide-co-caprolactone), poly(L-lactide-co-caprolactone), poly(D-lactide-co-caprolactone), poly(D,L-lactide), poly(D-lactide), poly(L-lactide), poly(esteramide), dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, polyetheretherketone, polymethylmethacrylate, silicone, hyaluronic acid, chitosan, or combinations thereof.

In some embodiments, the device has a thickness of from 0.01 mm to 5 mm, or from about 0.01 mm to about 2 mm, or 0.01 mm to about 1 mm. In some embodiments, the device has a length of about 0.01 mm to about 300 mm or about 0.01 mm to 200 mm or about 0.01 mm to about 150 mm.

In some embodiments, the diameter of the device can range from 0.01 mm to 10 mm. In some embodiments, the diameter of the device can range from 0.01 mm to 5 mm, 0.01 mm to 3 mm or 0.01 mm to 1 mm.

In some embodiments, a variety of bioabsorbable polymers can be used to make the device. Examples of suitable biocompatible, bioabsorbable polymers include aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biomolecules (i.e., biopolymers such as elastin, bioabsorbable starches, etc.) or blends thereof. Polyesters include, but are not limited to, homopolymers and copolymers of lactide (which includes lactic acid, D-, L- and meso lactide), glycolide (including glycolic acid), caprolactone, p-dioxanone (1,4-dioxan-2-one), trimethylene carbonate (1,3-dioxan-2-one), alkyl derivatives of trimethylene carbonate, delta-valerolactone, beta-butyrolactone, gamma-butyrolactone, epsilon-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan- 2-one 2,5-diketomorpholine, pivalolactone, alpha-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one or polymer blends thereof.

In some embodiments, the depots may be of different sizes depending on the procedure being performed and the implant site. Depots (e.g., fiber, strips, pellet, etc.) can range in size from about 0.01 to about 35 mm.

In some embodiments, the depot may be made by injection molding, compression molding, blow molding, thermoforming, die pressing, slip casting, electrochemical machining, laser cutting, water-jet machining, electrophoretic deposition, powder injection molding, sand casting, shell mold casting, lost tissue scaffold casting, plaster-mold casting, ceramic-mold casting, investment casting, vacuum casting, permanent-mold casting, slush casting, pressure casting, die casting, centrifugal casting, squeeze casting, rolling, forging, swaging, extrusion, shearing, spinning, powder metallurgy compaction or combinations thereof. In some embodiments, the depot is an injectable suspension or a super saturated injectable suspension.

In some embodiments, a therapeutic agent (including one or more imidazoline compounds such as clonidine) may be disposed on or in the device by hand by soaking, electrospraying, ionization spraying or impregnating, vibratory dispersion (including sonication), nozzle spraying, compressed-air-assisted spraying, brushing and/or pouring.

In some embodiments, the depot may comprise sterile and/or preservative free material. The depot can be implanted by hand or machine in procedures such as for example, laparoscopic, arthroscopic, neuroendoscopic, endoscopic, rectoscopic procedures or the like. In some embodiments, the depot can be made from a sponge material that can be spray coated or embedded with the imidazoline compound (e.g., clonidine), and as the sponge material degrades, the imidazoline compound (e.g., clonidine) is released.

In some embodiments, the depot is in a cylindrical form, however, alternate shapes and configurations may be contemplated. In further exemplary embodiments, the depot may be a narrow tube for delivery through a catheter. For example, the depot may be delivered percutaneously using a catheter through which it is inserted. Thus, the depot may have dimensions suitable for receipt in the catheter. Optionally, the depot may be stiffened to facilitate insertion into the catheter. Such stiffening may be achieved through choice of material for the depot, by treating the material of the device, or other. In some embodiments, the depot may be coated with a material to facilitate sliding engagement with the catheter.

In certain embodiments, the length of the depot will range from about 0.01 mm to about 35 mm, the width will range from about 0.01 mm to about 15 mm, and the thickness will range from about 0.01 mm to about 0.3 mm. In some embodiments, the length may range from about 0.01 to about 15 mm, the width may range from about 0.01 to about 5 mm, and the thickness may range from about 0.01 mm to about 15 mm.

In some embodiments, the depot has a modulus of elasticity in the range of about $1 \times 10^2$ to about $6 \times 10^5$ dynes/cm$^2$, or $2 \times 10^4$ to about $5 \times 10^5$ dynes/cm$^2$, or $5 \times 10^4$ dynes/cm$^2$ to about $5 \times 10^5$ dynes/cm$^2$.

In some embodiments, the depot may comprise a polymer having a molecular weight, as shown by the inherent viscosity, from about 0.10 dL/g to about 1.2 dL/g or from about 0.10 dL/g to about 0.40 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.55 dL/g, about 0.50 to about 0.70 dL/g, about 0.55 to about 0.6 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 dL/g, about 1.1 to about 1.3 dL/g, about 1.2 to about 1.4 dL/g, about 1.3 to about 1.5 dL/g, about 1.4 to about 1.6 dL/g, about 1.5 to about 1.7 dL/g, about 1.6 to about 1.8 dL/g, about 1.7 to about 1.9 dL/g, or about 1.8 to about 2.1 dL/g.

In some embodiments, the depot may comprise a viscosity enhancing agent such as, for example, hydroxypropyl cellulose, hydroxypropyl methylcellulose, hydroxyethyl methylcellulose, carboxymethylcellulose and salts thereof, Carbopol, poly-(hydroxyethyl-methacrylate), poly-(methoxyethylmethacrylate), poly(methoxyethoxyethyl-methacrylate), polymethyl-methacrylate (PMMA), methyl-methacrylate (MMA), gelatin, polyvinyl alcohols, propylene glycol, mPEG, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

In some embodiments, the depot may comprise gelatin, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. In some embodiments, the depot may comprise polyvinyl alcohol, acrylamides such as polyacrylic acid and poly (acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof.

In various embodiments, rather than directly admixing the therapeutic agent into the depot, microspheres may be dispersed within the device, the microspheres being loaded with clonidine. In one embodiment, the microspheres provide for a sustained release of the clonidine.

Microspheres, much like a fluid, may disperse relatively quickly, depending upon the surrounding tissue type, and hence disperse the clonidine. In some situations, this may be desirable; in others, it may be more desirable to keep the clonidine tightly constrained to a well-defined target site. In some embodiments, the composition can comprise nanospheres having a diameter of from about 1 to about 500 nanometers. The present invention also contemplates the use of adherent gel or adhesive to so constrain the device close to the target tissue site. In this embodiment, an adherent gel or adhesive is used to anchor the device to the target tissue site. The adherent gel or adhesive can, like the depot, also have the therapeutic agent disposed within it. In this way, the depot and the adhesive release the therapeutic agent (e.g., clonidine) at or near the target tissue site.

Gel

In various embodiments, the imidazoline compound (e.g., clonidine) is administered in a gel. The gel may have a pre-dosed viscosity in the range of about 1 to about 2000 centipoise (cps), 1 to about 200 cps, or 1 to about 100 cps. In some embodiments, the gel may have a pre-dosed viscosity of 1, 5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250, 1275, 1300, 1325, 1350, 1375, 1400, 1425, 1450, 1475, 1500, 1525, 1550, 1575, 1600, 1625, 1650, 1675, 1700, 1725, 1750, 1775, 1800, 1825, 1850, 1875, 1900, 1925, 1950, 1975 or 2000 cps. After the gel is administered to the target site, the viscosity of the gel will increase and the gel will have a modulus of elasticity (Young's modulus) in the range of about $1\times-10^2$ to about $6\times10^5$ dynes/cm$^2$, or $2\times10^4$ to about $5\times10^5$ dynes/cm$^2$, or $5\times10^4$ to about $5\times10^5$ dynes/cm$^2$.

In one embodiment, the gel is an adherent gel comprising the imidazoline compound (e.g., clonidine) that is evenly distributed throughout the gel. The gel may be of any suitable type and should be sufficiently viscous so as to prevent the gel from migrating from the targeted delivery site once deployed; the gel should, in effect, "stick" or adhere to the targeted tissue site. The gel may, for example, solidify upon contact with the targeted tissue or after deployment from a targeted delivery system. The targeted delivery system may be, for example, a syringe, a catheter, needle or cannula or any other suitable device. The targeted delivery system may inject the gel into or on the targeted tissue site. The therapeutic agent may be mixed into the gel prior to the gel being deployed at the targeted tissue site. In various embodiments, the gel may be part of a two-component delivery system and when the two components are mixed, a chemical process is activated to form the gel and cause it to stick or to adhere to the target tissue.

In various embodiments, a gel is provided, which hardens or stiffens after delivery. Typically, hardening gel formulations may have a pre-dosed modulus of elasticity in the range of about $1\times-10^2$ to about $3\times10^5$ dynes/cm$^2$, or $2\times10^4$ to about $2\times10^5$ dynes/cm$^2$, or $5\times10^4$ to about $1\times10^5$ dynes/cm$^2$. The post-dosed hardening gels (after delivery) may have a rubbery consistency and have a modulus of elasticity in the range of about $1\times-10^2$ to about $2\times10^6$ dynes/cm$^2$, or $1\times10^5$ to about $7\times10^5$ dynes/cm$^2$, or $2\times10^5$ to about $5\times10^5$ dynes/cm$^2$.

In various embodiments, for those gel formulations that contain a polymer, the polymer concentration may affect the rate at which the gel hardens (e.g., a gel with a higher concentration of polymer may coagulate more quickly than gels having a lower concentration of polymer). In various embodiments, when the gel hardens, the resulting matrix is solid but is also able to conform to the irregular surface of the tissue (e.g., recesses and/or projections in bone).

The percentage of polymer present in the gel may also affect the viscosity of the polymeric composition. For example, a composition having a higher percentage by weight of polymer is typically thicker and more viscous than a composition having a lower percentage by weight of polymer. A more viscous composition tends to flow more slowly. Therefore, a composition having a lower viscosity may be preferred in some instances. In some embodiments, the polymer comprises 20 wt. % to 90 wt. % of the formulation. In some embodiments, the polymer comprises 40 wt. % to 95 wt. % of the formulation. In some embodiments, the polymer comprises 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 or 95 wt. % of the formulation.

In various embodiments, the molecular weight of the gel can be varied by many methods known in the art. The choice of method to vary molecular weight is typically determined by the composition of the gel (e.g., polymer, versus non-polymer). For example, in various embodiments, when the gel comprises one or more polymers, the degree of polymerization can be controlled by varying the amount of polymer initiators (e.g. benzoyl peroxide), organic solvents or activator (e.g. DMPT), crosslinking agents, polymerization agent, incorporation of chain transfer or chain capping agents and/or reaction time.

Suitable gel polymers may be soluble in an organic solvent. The solubility of a polymer in a solvent varies depending on the crystallinity, hydrophobicity, hydrogen-bonding and molecular weight of the polymer. Lower molecular weight polymers will normally dissolve more readily in an organic solvent than high-molecular weight polymers. A polymeric gel that includes a high molecular weight polymer tends to coagulate or solidify more quickly than a polymeric composition that includes a low-molecular weight polymer. Polymeric gel formulations that include high molecular weight polymers, also tend to have a higher solution viscosity than a polymeric gel that includes low-molecular weight polymers. In various embodiments, the molecular weight of the polymer can be a wide range of values.

The average molecular weight of the polymer can be from about 1,000 to about 10,000,000; or about 1,000 to about 1,000,000; or about 5,000 to about 500,000; or about 10,000 to about 100,000; or about 20,000 to 50,000 g/mol. In some embodiments, the molecular weight of the polymer is 1,000, 2,000, 3,000, 4,000, 5,000, 6,000, 7,000, 8,000, 9,000, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, 125,000, 150,000, 175,000, 200,000, 225,000, 250,000, 275,000, 300,000, 325, 000, 350,000, 375,000, 400,000, 425,000, 450,000, 475,000, 500,000, 525,000, 550,000, 575,000, 600,000, 625,000, 650, 000, 675,000, 700,000, 725,000, 750,000, 775,000, 800,000, 825,000, 850,000, 875,000, 900,000, 925,000, 950,000, 975, 000 and/or 1,000,000 Daltons.

When the gel is designed to be a flowable gel, it can vary from low viscosity, similar to that of water, to high viscosity, similar to that of a paste, depending on the molecular weight and concentration of the polymer used in the gel. The viscosity of the gel can be varied such that the polymeric composition can be applied to a patient's tissues by any convenient technique, for example, by brushing, dripping, injecting, or painting. Different viscosities of the gel will depend on the technique used to apply the composition.

In various embodiments, the gel has an inherent viscosity (abbreviated as "I.V." and units are in deciliters/gram), which is a measure of the gel's molecular weight and degradation time (e.g., a gel with a high inherent viscosity has a higher molecular weight and may have a longer degradation time). Typically, when the polymers have similar components but different molecular weights, a gel with a high molecular weight provides a stronger matrix and the matrix takes more time to degrade. In contrast, a gel with a low molecular weight degrades more quickly and provides a softer matrix. In various embodiments, the polymer of the depot or the depot has a molecular weight, as shown by the inherent viscosity, from about 0.10 dL/g to about 1.2 dL/g or from about 0.10 dL/g to about 0.40 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.50 dL/g, about 0.50 to about 0.70 dL/g, about 0.60 to about 0.80 dL/g, about 0.70 to about 0.90 dL/g, and about 0.80 to about 1.00 dL/g.

In various embodiments, the gel can have a viscosity of about 300 to about 5,000 centipoise (cp). In other embodiments, the gel can have a viscosity of from about 5 to about 300 cps, from about 10 cps to about 50 cps, or from about 15 cps to about 75 cps at room temperature. The gel may optionally have a viscosity enhancing agent such as, for example, hydroxypropyl cellulose, hydroxypropyl methylcellulose, hydroxyethyl methylcellulose, carboxymethylcellulose and salts thereof, Carbopol, poly-(hydroxyethylmethacrylate), poly-(methoxyethylmethacrylate), poly(methoxyethoxyethyl methacrylate), polymethylmethacrylate (PMMA), methylmethacrylate (MMA), gelatin, polyvinyl alcohols, propylene glycol, mPEG, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

In various embodiments, the gel is a hydrogel made of high molecular weight biocompatible elastomeric polymers of synthetic or natural origin. A desirable property for the hydrogel to have is the ability to respond rapidly to mechanical stresses, particularly shears and loads, in the human body.

Hydrogels obtained from natural sources are particularly appealing because they are more likely to be biocompatible for in vivo applications. Suitable hydrogels include natural hydrogels, such as for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly (acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof. The hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyether-urethane, or a combination thereof.

In various embodiments, rather than directly admixing the therapeutic agent into the gel, microspheres may be dispersed within the gel, the microspheres being loaded with anabolic agent. In one embodiment, the microspheres provide for a sustained release of the anabolic agent. In yet another embodiment, the gel, which is biodegradable, prevents the microspheres from releasing the anabolic agent; the microspheres thus do not release the anabolic agent until they have been released from the gel. For example, a gel may be deployed around a target tissue site (e.g., a nerve root). Dispersed within the gel may be a plurality of microspheres that encapsulate the desired therapeutic agent. Certain of these microspheres degrade once released from the gel, thus releasing the anabolic agent.

Microspheres, much like a fluid, may disperse relatively quickly, depending upon the surrounding tissue type, and hence disperse the anabolic agent. In some situations, this may be desirable; in others, it may be more desirable to keep the anabolic agent tightly constrained to a well-defined target site. The present invention also contemplates the use of adherent gels to so constrain dispersal of the therapeutic agent. These gels may be deployed, for example, at or near the injury, in a disc space, in a spinal canal, or in surrounding tissue.

Liposomes

Liposome Formulation/Liposomal Encapsulation

In one embodiment, the imidazoline compound (e.g., clonidine) is encapsulated in a liposome. The imidazoline compound (e.g., clonidine) may be liposomally encapsulated by contacting an unloaded liposome with the clonidine in an exterior aqueous solution at an exterior aqueous solution pH. In some embodiments, the unloaded liposome comprises an interior cavity aqueous solution with an interior cavity pH that is higher than the exterior aqueous solution pH. The imidazoline compound (e.g., clonidine) is then moved from the exterior aqueous solution to the interior cavity thereby forming liposomally encapsulated imidazoline compound (e.g., clonidine).

In some embodiments, a liposome formulation is provided for liposome encapsulation. The liposomes can be suspended in a solution, such as, for example, 0.9% sodium chloride solution, sterile water for injection, dextrose or a combination thereof. The imidazoline compound (e.g., clonidine) may then be added to the liposome/solution in a concentration of about 0.5 µg/mL to 10,000 µg/mL. In some embodiments, the solution can contain other ingredients such as, for example, 4.7 mg/mL of cholesterol; 0.9 mg/mL of 1, 2-dipalmitoyl-sn-glycero-3 phospho-rac-(1-glycerol) (DPPG); 2.0 mg/mL of tricaprylin; and 8.2 mg/mL of 1, 2-dierucoylphosphatidylcholine (DEPC). In some embodiments, the pH of the formulation is in the range of about 5.8 to 7.4.

The liposome formulation as described above is shown in Table 1 below.

TABLE 1

| Ingredient/Feature | Amount/Range |
| --- | --- |
| Clonidine | 0.5 µg to 10,000 µg/mL |
| 0.9% Sodium chloride solution | N/A |
| Inactive ingredients: | |
| Cholesterol; | 4.7 mg/mL |
| 1,2-dipalmitoyl-sn-glycero-3 phospho-rac-(1-glycerol) (DPPG); | 0.9 mg/mL |
| Tricaprylin; and | 2.0 mg/mL |
| 1,2-dierucoylphosphatidylcholine (DEPC) | 8.2 mg/mL |
| pH | 5.8-7.4 |

In some embodiments, liposome encapsulation of the imidazoline compound (e.g., clonidine) can facilitate enhanced drug efficacy while reducing toxicity. In some embodiments, liposome encapsulation of the imidazoline compound (e.g., clonidine) provides burst and/or a sustained release of the imidazoline compound (e.g., clonidine) to provide nerve block at the target tissue site.

In some embodiments, the liposome encapsulated imidazoline compound (e.g., clonidine) has a diameter in the range of about 0.1 to about 20 µm. In some embodiments, the liposome encapsulated imidazoline compound (e.g., clonidine) has a diameter in the range of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19 to about 20 µm.

In some embodiments, a lipid can comprise the liposome, including, but not limited to, cationic lipids, zwitterionic lipids, neutral lipids, or anionic lipids. In some embodiments, the lipid can include fats, waxes, steroids, cholesterol, fat-soluble vitamins, monoglycerides, diglycerides, phospholipids, sphingolipids, glycolipids, cationic or anionic lipids, derivatized lipids, or the like.

In some embodiments, a phospholipid can comprise the liposome, including, but not limited to phosphatidylcholine (PC), phosphatidic acid (PA), phosphatidylethanolamine (PE), phosphatidylglycerol (PG), phosphatidylserine (PS), and phosphatidylinositol (PI), dimyristoyl phosphatidyl choline (DMPC), distearoyl phosphatidyl choline (DSPC), dioleoyl phosphatidyl choline (DOPC), dipalmitoyl phosphatidyl choline (DPPC), dimyristoyl phosphatidyl glycerol (DMPG), distearoyl phosphatidyl glycerol (DSPG), dioleoyl phosphatidyl glycerol (DOPG), dipalmitoyl phosphatidyl glycerol (DPPG), dimyristoyl phosphatidyl serine (DMPS), distearoyl phosphatidyl serine (DSPS), dioleoyl phosphatidyl serine (DOPS), dipalmitoyl phosphatidyl serine (DPPS), dioleoyl phosphatidyl ethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), 1,2-dielaidoyl-sn-glycero-3-phophoethanolamine (transDOPE), and cardiolipin. In some embodiments, lipid extracts, such as for example, egg PC, heart extract, brain extract, liver extract, and soy PC, can be used for encapsulation. In certain embodiments, the lipids can include derivatized lipids, such as PEGylated lipids. In some embodiments, derivatized lipids include, but are not limited to DSPE-PEG2000, cholesterol-PEG2000, DSPE-polyglycerol, or any combination thereof.

In some embodiments, cationic lipids comprise the liposome which contain positively charged functional groups under physiological conditions. In some embodiments, the cationic lipids include, but are not limited to N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N-[1-(2,3,-ditetradecyloxy)propyl]-N,N-dimethyl-N-hydroxyethylammonium bromide (DMRIE), N-[1-(2,3, dioleyloxy)propyl]-N,N-dimethyl-N-hydroxy ethylammonium bromide (DORIE), 3β-[N—(N', N'-dimethylaminoethane) carbamoyl] cholesterol (DC-Chol), dimethyldioctadecylammonium (DDAB) and N,N-dimethyl-2,3-dioleyloxy)propylamine (DODMA).

In some embodiments, the liposomes may include between about 1 to 20 types of lipids. In some embodiments, the liposomes may include about 1, 2, 3, 4, 5, 6, 7, 8, 9, 10, 11, 12, 13, 14, 15, 16, 17, 18, 19 or 20 lipids.

Device Delivery

It will be appreciated by those with skill in the art that the depot (e.g., device) can be administered to the target site using a "cannula" or "needle" that can be a part of a drug delivery device e.g., a syringe, a gun drug delivery device, or any medical device suitable for the application of a drug to a targeted organ or anatomic region. The cannula or needle of the device is designed to cause minimal physical and psychological trauma to the patient.

In some embodiments, the depot can be sutured to a target tissue site using a suturing needle. The dimensions of the needle, among other things, will depend on the site for implantation. For example, the width of the muscle planes in different surgical procedures can vary from 1-40 cm. Thus, the needle, in various embodiments, can be designed for these specific areas.

In various embodiments, like the depot, the cannula or needle includes dose radiographic markers that indicate location at or near the site beneath the skin, so that the user may accurately position the depot (e.g., device) at or near the site using any of the numerous diagnostic imaging procedures. Such diagnostic imaging procedures include, for example, X-ray imaging or fluoroscopy. Examples of such radiographic markers include, but are not limited to, barium, bismuth, tantalum, tungsten, iodine, and/or metal beads or particles.

In various embodiments, the needle or cannula may include a transparent or translucent portion that can be visualizable by ultrasound, fluoroscopy, X-ray, or other imaging techniques. In such embodiments, the transparent or translucent portion may include a radiopaque material or ultrasound responsive topography that increases the contrast of the needle or cannula relative to the absence of the material or topography.

The depot may be sterilizable. In various embodiments, one or more components of the device are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the device is included in a gel.

Other methods may also be used to sterilize the depot (e.g., device) and/or one or more components of the device, including, but not limited to, gas sterilization, such as, for example, with ethylene oxide or steam sterilization.

In various embodiments, a kit is provided that may include additional parts along with the depot combined together to be used to implant the depot. The kit may include the pharmaceutical composition in a first compartment. The second compartment may include a canister holding the pharmaceutical composition and any other instruments needed for the localized drug delivery. A third compartment may include gloves, drapes, wound dressings and other procedural supplies for maintaining sterility of the implanting process, as well as an instruction booklet. A fourth compartment may include additional cannulas and/or needles. A fifth compartment may include an agent for radiographic imaging. Each tool may be separately packaged in a plastic pouch that is radiation sterilized. A cover of the kit may include illustrations of the implanting procedure and a clear plastic cover may be placed over the compartments to maintain sterility. In some embodiments, a kit is provided with instruction to use an injectable drug from another kit.

In various embodiments, a method for delivering a therapeutic agent into a site of a patient is provided, the method comprising inserting a needle at or near a target tissue site and suturing the depot at the target site beneath the skin of the patient. In this way, unwanted migration of the depot away from the target site is reduced or eliminated.

In some embodiments, the depot can be delivered to any site beneath the skin, including, but not limited to, at least one muscle, ligament, tendon, cartilage, spinal disc, spinal foraminal space, near the spinal nerve root, a dorsal root ganglion, peripheral nerve fiber, peripheral nerve root, connective tissue, fascia, subcutaneous space, or spinal canal. In some embodiments, the depot in injectable form can be delivered under the epineurium of a medial genicular nerve for treatment of acute medial knee pain, as shown in FIG. 1. The depot in injectable form can also be an intraneural depot that is administered beneath perineurium membrane.

In some embodiments, it is preferable to co-administer an imidazoline compound such as clonidine with an antagonist to counteract undesirable effects, for example the blood pressure decrease that can be caused by clonidine. Exemplary antagonists include but are not limited to phentolamine, yohimbine, tolazoline and piperoxane. Additionally, compounds such as 5-fluorodeoxyuridine (FUDR) and 3,4 dehydroprolene may also be included. These compounds may prevent or reduce glial and fibroblastic scar formation associated with some types of surgeries.

Another embodiment is directed to a method for treating a mammal suffering from pain, said method comprising administering a therapeutically effective amount of an imidazoline compound at a target site beneath the skin. The imidazoline compound (or pharmaceutically acceptable salt) may for example be administered locally to the target tissue site disposed within or on a device. In some embodiments, the imidazoline compound depot (e.g., device) is administered by placement into an open patient cavity during surgery. In some embodiments, the imidazoline compound is clonidine.

Method of Making the Device

In various embodiments, the depot comprising the imidazoline compound such as clonidine can be made by combining a biodegradable polymer and a therapeutically effective amount of clonidine or pharmaceutically acceptable salt thereof and forming the implantable device from the combination.

Various techniques are available for forming at least a portion of a depot from the biocompatible polymer(s), therapeutic agent(s), and optional materials, including solution processing techniques and/or thermoplastic processing techniques. Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot (e.g., device) to obtain the desired release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise, one or more of the following: clonidine and other therapeutic agent(s) and other optional additives such as radiographic agent(s), etc. in dissolved or dispersed form. This results in a polymeric device region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot (e.g., device) or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: clonidine, optional additional therapeutic agent(s), radiographic agent(s), and so forth. The resulting mixture is then shaped into an implantable device. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, clonidine may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the therapeutic agent, if it were present. This precompounded material is then mixed with therapeutic agent under conditions of lower temperature and mechanical shear, and the resulting mixture is shaped into the imidazoline compound (e.g., clonidine) containing device. Conversely, in another embodiment, the biocompatible polymer can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the device.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot (e.g., device) is formed comprising PLGA or PLA polymer, a radio-opacifying agent (e.g., bismuth subcarbonate), and a therapeutic agent prone to degradation by heat and/or mechanical shear (e.g., clonidine), in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min). It is noted that this processing temperature is well below the melting points of clonidine because processing at or above these temperatures will result in substantial therapeutic agent degradation. It is further noted that in certain embodiments, the processing temperature will be below the melting point of all bioactive compounds within the composition, including the therapeutic agent. After compounding, the resulting depot (e.g., device) is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing device (the pre-existing device can be formed using a variety of techniques including solution and thermoplastic processing techniques, and it can comprise a variety of additives including a radio-opacifying agent and/or viscosity enhancing agent), whereupon the therapeutic agent is imbibed on or in the device. As above, the resulting solid material can then be granulated for further processing, if desired.

Typically, an extrusion process may be used to form the device comprising a biocompatible polymer(s), therapeutic agent(s) and radio-opacifying agent(s). Co-extrusion may also be employed, which is a shaping process that can be used to produce a device comprising the same or different layers or regions (for example, a structure comprising one or more polymeric device layers or regions that have permeability to fluids to allow immediate and/or sustained drug release). Multi-region depots (e.g., devices) can also be formed by other processing and shaping techniques such as co-injection or sequential injection molding technology.

In various embodiments, the depot (e.g., device) that may emerge from the thermoplastic processing is cooled. Examples of cooling processes include air cooling and/or immersion in a cooling bath. In some embodiments, a water bath is used to cool the extruded depot (e.g., device). However, where a water-soluble therapeutic agent such as clonidine is used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot (e.g., device) surface, thus controlling or minimizing a high drug dose "initial burst" or "bolus dose" upon implantation or insertion if this is release profile is not desired.

In various embodiments, the device can be prepared by mixing or spraying the drug with the polymer and then molding the depot (e.g., device) to the desired shape. In various embodiments, the imidazoline compound (e.g., clonidine) is used and mixed or sprayed with the PLGA or PEG550 polymer, and the resulting depot (e.g., device) may be formed by extrusion and dried.

In various embodiments, there is a pharmaceutical formulation comprising: clonidine, wherein the clonidine comprises from about 0.1 wt. % to about 40 wt. % of the formulation, and at least one biodegradable polymer. In some embodiments, the clonidine comprises from about 3 wt. % to about 20 wt. %, about 3 wt. % to about 18 wt. %, about 5 wt. % to about 15 wt. %, 0.1 wt % to about 10 wt %, about 0.1 wt % to about 3 wt %, or about 7.5 wt. % to about 12.5 wt. % of the formulation. By way of example, when using a 5%-15% clonidine composition, the mole ratio of clonidine to polymer would be from approximately 16-53 when using an approximately 80,000 Da polymer that has a 267 grams/mole ratio. By way of another example, when using a 5%-15% clonidine base in the composition, the mole ratio of clonidine base to polymer would be from approximately 18-61 with a mole mass of 230 g/mol. Alternatively, the pharmaceutical formulation comprises a different imidazoline compound instead of clonidine.

In some embodiments, the imidazoline compound (e.g., clonidine) can be in the formulation in an amount of about 1%, 5%, 10%, 15%, 20%, 25%, 30%, 35%, or 40% by weight based on the total weight of the formulation.

In some embodiments, the device comprises at least one biodegradable material in a wt % of about 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 76%, 75%, 74%, 73%, 72%, 71%, 70%, 65%, 60%, 55%, 50%, 45%, 35%, 25%, 20%, 15%, 10%, or 5% based on the total weight of the depot (e.g., device) and the remainder is active and/or inactive pharmaceutical ingredients.

In some embodiments, at least 75% of the particles have a size from about 0.5 micrometer to about 100 micrometers. In some embodiments, at least 85% of the particles have a size from about 0.5 micrometers to about 100 micrometers. In some embodiments, at least 95% of the particles have a size from about 0.5 micrometer to about 100 micrometers. In some embodiments, all of the particles have a size from about 0.5 micrometer to about 100 micrometers. In some embodiments, at least 80% of the particles have a size from 2 microns to about 50 microns on a volume basis.

In some embodiments, the device comprises about 95 wt % poly(D,L-lactide) and 5 wt % clonidine HCl where the polymer has an ester end group and 50,000-70,000 Da MW and an IV 0.45-0.55 dL/g and has a burst release of under 10% of the amount of drug in the depot (e.g., device) within 24 hours (e.g., 5-10 wt %) or 2-40 mcg in 24 hours. This formulation has 50% of total cumulative dose remaining for at least 60 days. About 80% of the particles in this depot (e.g., device) including the clonidine are from about 5 to about 150 microns or 5-100 microns. The depot (e.g., device) releases about 0.5 mcg/day up to about 5 mcg/day of clonidine in 24 hours and then continues release for 70 days.

In some embodiments, the device comprises about 92 wt % poly(D,L-lactide) and 8 wt % clonidine HCl where the polymer has an ester end group and the polymer comprises 50,000-70,000 Da MW and an IV of about 0.45-0.55 dL/g and has a burst release of under 10% of the amount of drug in the depot (e.g., device) within 24 hours (e.g., 5-10%) or 5-6 mcg in 24 hours and then 1 to 20 mcg/day with a constant release for about 50 days, and then about 0.1 mcg to about 10 mcg/day for 70 days. This formulation has 50% of total cumulative dose remaining for at least 30-42 days and less than 80% cumulative drug release by 70 days. About 80% of the particles in this depot (e.g., device) including the clonidine are from about 5 to about 150 microns or 5-100 microns.

In some embodiments, the device comprises about 85 wt % poly(D,L-lactide) and 15 wt % clonidine HCl where the polymer has an ester end group and the polymer comprises 50,000-70,000 Da MW and an IV of about 0.45-0.55 dL/g and has a burst release of under 10% of the amount of drug in the depot (e.g., device) within 24 hours (e.g., 5-10%) or 20-150 mcg in 24 hours and then 5 to 80 mcg/day with a constant release for about 30 days, and then about 0.1 mcg to about 5 mcg/day for 70 days. This formulation has about 80% of total cumulative dose released within 35 days and 20% over several months. About 80% of the particles in this depot (e.g., device) including the clonidine are from about 5 to about 150 microns or 5-100 microns.

In some embodiments, there is a pharmaceutical formulation comprising clonidine, wherein the clonidine is in a mixture of clonidine hydrochloride and clonidine base and the mixture comprises from about 0.1 wt. % to about 30 wt. % of the formulation and a polymer comprises at least 70% of the formulation. In some embodiments, the polymer in this formulation is polyorthoester.

In some embodiments, the formulation comprises a device that comprises a biodegradable polyorthoester. The mechanism of the degradation process of the polyorthoester can be hydrolytical or enzymatical in nature, or both. In various embodiments, the degradation can occur either at the surface of the device (heterogeneous or surface erosion) or uniformly throughout the drug delivery system depot (e.g., device) (homogeneous or bulk erosion). Polyorthoester can be obtained from A.P. Pharma, Inc. (Redwood City, Calif.) or through the reaction of a bis(ketene acetal) such as 3,9-diethylidene-2,4,8,10-tetraoxospiro[5,5]undecane (DETOSU) with suitable combinations of diol(s) and/or polyol(s) such as 1,4-trans-cyclohexanedimethanol and 1,6-hexanediol or by any other chemical reaction that produces a polymer comprising orthoester moieties.

In some embodiments, there is a higher loading of clonidine, e.g., at least 5 wt. %, at least 10 wt. %, at least 15 wt. %, at least 20 wt. %, at least 30 wt. %, at least 40 wt. %, at least 50 wt. %, or at least 60 wt. %.

A strategy of triangulation may be effective when administering these pharmaceutical formulations. Thus, a plurality (at least two, at least three, at least four, at least five, at least six, at least seven, etc.) devices comprising the pharmaceutical formulations may be placed around the target tissue site (also known as the pain generator or pain generation site) such that the target tissue site falls within a region that is either between the formulations when there are two, or within an area whose perimeter is defined by a set of plurality of formulations.

In some embodiments, the formulations are slightly rigid with varying length, widths, diameters, etc. For example, certain formulations may have a diameter of 0.50 mm and a length of 4 mm. It should be noted that particle size may be altered by techniques such as mort and pestle, jet-drying or jet milling.

Imidazoline Compound Dosage

The imidazoline compound (e.g., clonidine) can be administered to produce nerve block and anesthesia in areas that do not have α2 adrenergic receptors. Anesthesia includes a state of temporary induced loss of pain sensation or awareness and may include relief from or prevention of pain. Nerve block includes a pain management technique involving the injection of an imidazoline compound at or near the area surrounding an affected nerve. The technique is used to treat pain by interrupting pain signals from a nerve to the brain. In some embodiments, the dosage of the imidazoline compound (e.g., clonidine) released from the depot or injected locally at or near the target tissue site may be from approximately 50 µg and 10,000 µg per hour and/or day to provide nerve block and local anesthesia at or near the target tissue site. In some embodiments, the dosage of imidazoline compound (e.g., clonidine) released from the depot or injected locally at or near the target tissue site may be from about 50 µg, 60, 70, 80, 90, 100, 200, 300, 400, 500, 600, 700, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 6,100, 6,200, 6,300, 6,400, 6,500, 6,600, 6,700, 6,800, 6,900, 7,000, 7,100, 7,200, 7,300, 7,400, 7,500, 7,600, 7,700, 7,800, 7,900, 8,000, 8,100, 8,200, 8,300, 8,400, 8,500, 8,600, 8,700, 8,800, 8,900, 9,000, 9,100, 9,200, 9,300, 9,400, 9,500, 9,600, 9,700, 9,800, 9,900 to about 10,000 µg per hour and/or day. In some embodiments, the amount of imidazoline compound (e.g., clonidine) is between approximately 100 µg and 500 µg/day or µg/hour. In some embodiments, the amount of imidazoline compound (e.g., clonidine) is between 200 and 400 µg/day.

In some embodiments, the therapeutically effective dosage amount (e.g., imidazoline compound dose) and the release rate profile are sufficient to reduce post-operative pain for a period of at least one day, for example, 1-2 days, 1-3 days, 1-4 days, 1-5 days, 1-6 days; 1-7 days, 1-8 days, 1-9 days, 1-10 days, 2-3 days, 2-4 days, 2-5 days, 2-6 days; 2-7 days, 2-8 days, 2-9 days, 2-10 days, 2-11 days, 3-4 days, 3-5 days, 3-6 days; 3-7 days, 3-8 days, 3-9 days, 3-10 days, or 3-11 days.

In some embodiments, the imidazoline compound (e.g., clonidine) in the device is designed for a bolus dose or burst dose within 1, 2, or 3 days after implantation to provide an immediate release of the clonidine for treatment of pain and/or inflammation.

In some embodiments, the imidazoline compound (e.g., clonidine) depot, composition or formulation can provide a dosage of from about 1.0 mg, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5, 60.0 mg of imidazoline compound (e.g., clonidine) per day.

In some embodiments, the imidazoline compound (e.g., clonidine) depot or formulation can provide a dosage of from about 100 mg, 125, 150, 175, 200, 225, 250, 275, 300, 325, 350, 375, 400, 425, 450, 475, 500, 525, 550, 575, to about 600 mg of imidazoline compound (e.g., clonidine) per day.

In some embodiments, the imidazoline compound (e.g., clonidine) depot, composition or formulation can provide a dosage of from about 1.0 mg/kg/day, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5 to about 60.0 mg/kg of imidazoline compound (e.g., clonidine) per hour and/or day.

EXAMPLES

The examples illustrate that clonidine can act directly on peripheral axons. The clonidine can be provided to the nerve to cause nerve block, which is suitable for providing local anesthesia and pain relief. The local anesthetic activity of clonidine is alpha adrenergic receptor independent.

Example 1

It has been hypothesized that direct effects on peripheral axons may contribute to clonidine's pain-relieving properties due to its direct effects on peripheral axons of the nerves. It is noted that alpha 2 adrenergic receptors are not expressed along the peripheral axons of the nerve. They are on nerve endings and in the spinal cord, where peripheral nerves synapse with interneurons in the dorsal horn. There also may be receptor-mediated effects on immunoinflammatory cells. Therefore, the anesthetic effect of clonidine is independent of alpha 2 adrenergic receptors. In this study, we show that clonidine, injected directly into the right sciatic nerve of the rat, blocked the ability of the nerve to propagate action potentials to the spinal cord. However, there was no effect on the left sciatic nerve. Moreover, pre-administration of a high-dose of a receptor antagonist had no effect on the anesthetic-like effects of clonidine. An anesthetic like effect was observed with clinically relevant doses of clonidine (<100 mcg). This is similar to what occurred with the positive control (2% lidocaine), where nerve function recovered over the course of approximately one hour, which is significant in the rat model and would equate to 24 hours of a nerve block in a human.

Example 2

Action potentials were measured before injecting clonidine and after administering clonidine. It was noted that action potentials were eliminated after injecting clonidine. 2 m Amp stimulation in the ankle causes the action potential to propagate up to the tibial nerves and then the sciatic nerve to the dorsal horn of the spinal cord in the rat model. Injecting 50 mcg or more of clonidine directly into nerve, eliminates the action potential. Duration of effect is proportional to dose, where 500 mcg lasts a lot longer than 50 mcg.

Figure 2:
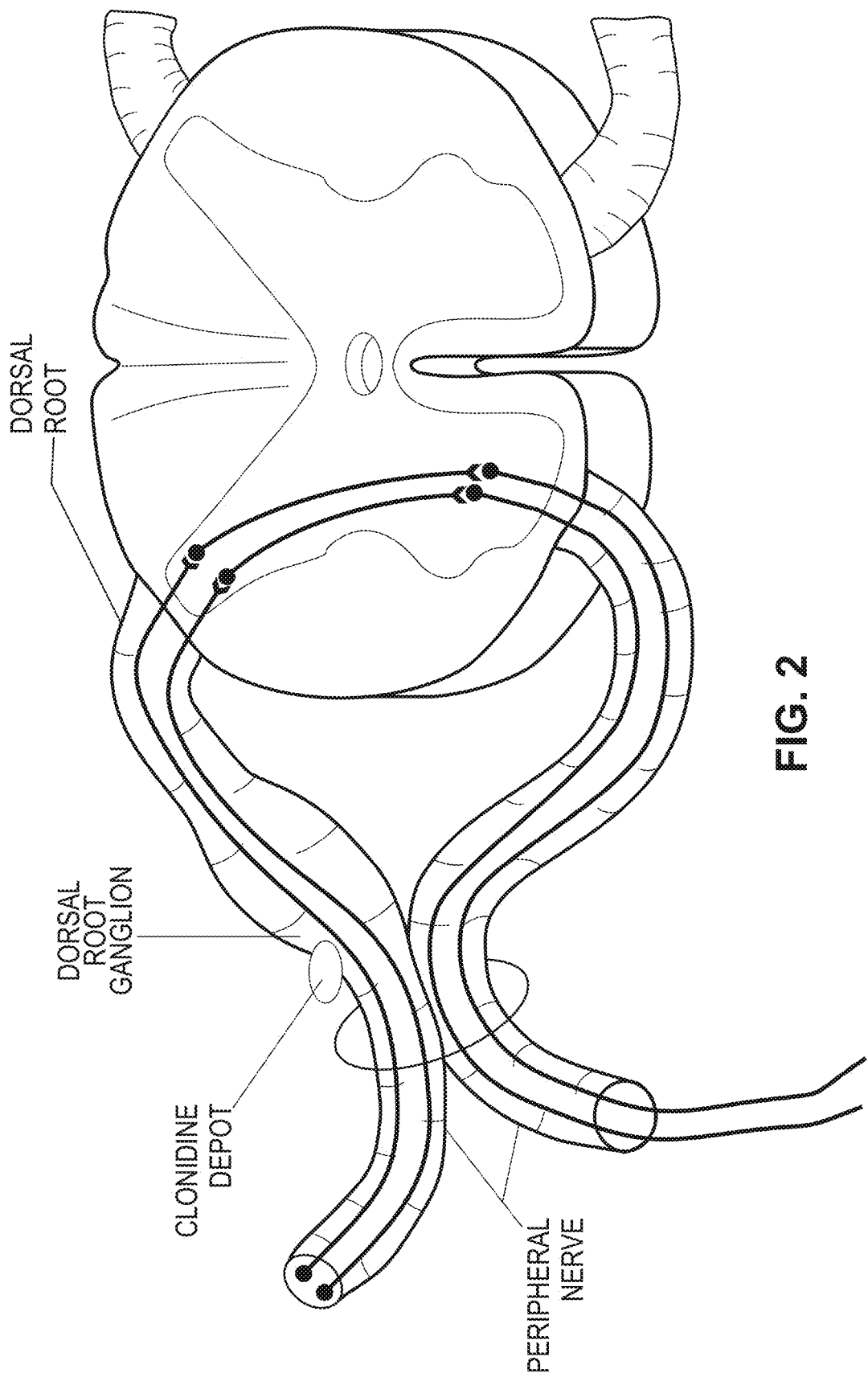
FIG. 2 illustrates a location that the pharmaceutical composition comprising clonidine provides nerve block and anesthesia extending outside of the spinal column to the dorsal root ganglion, peripheral nerve fiber and peripheral nerve root. These locations are deplete of alpha adrenergic membrane receptors and thus the clonidine nerve blockade is alpha adrenergic receptor independent.

FIG. 2 illustrates the location that the clonidine provides nerve block and anesthesia extending outside of the spinal column to the dorsal root ganglion, peripheral nerve fiber and peripheral nerve root. These locations are deplete of alpha adrenergic receptors and thus the clonidine nerve blockade is alpha adrenergic receptor independent.

Example 3

Figure 3:
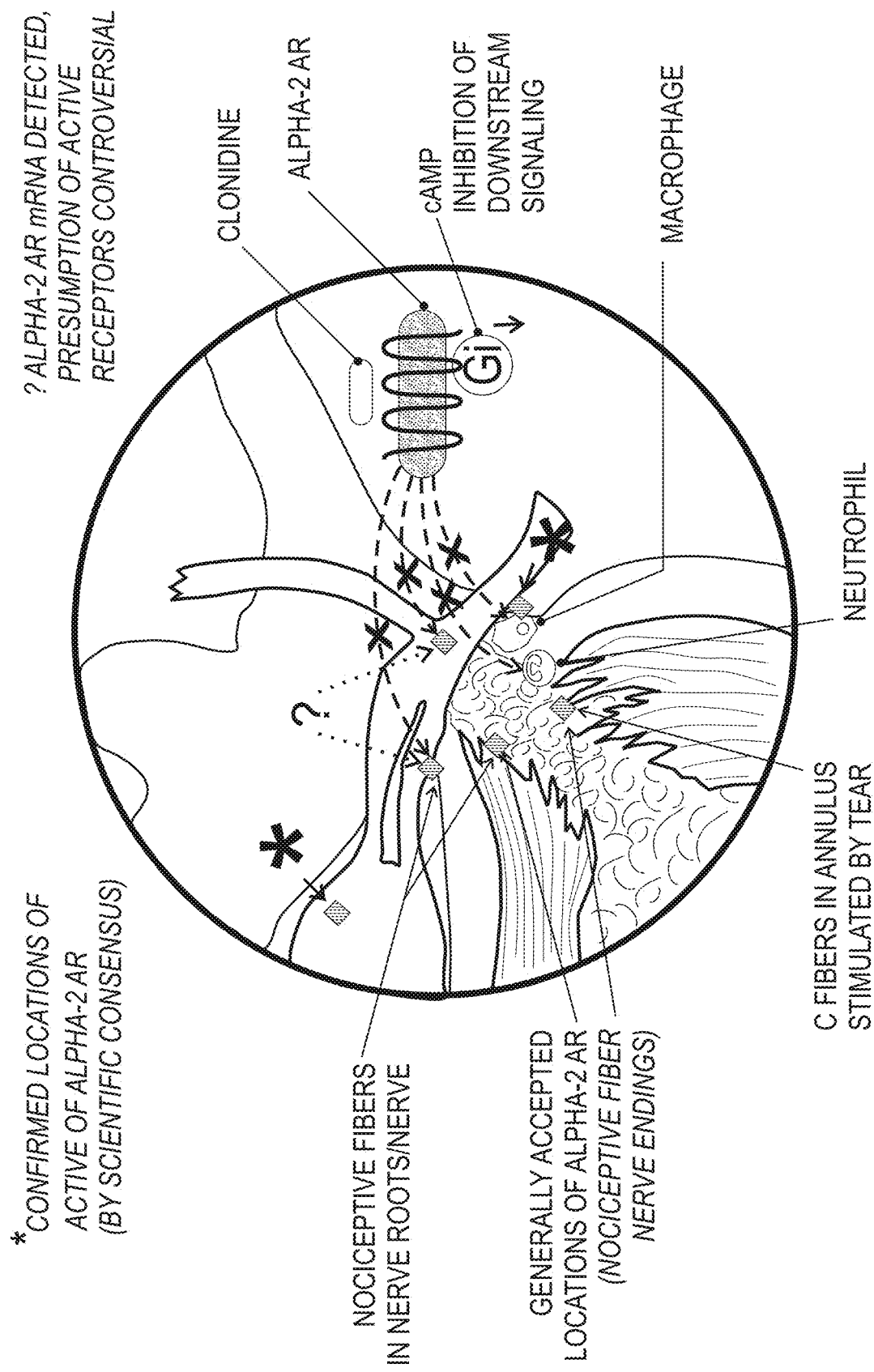
FIG. 3 illustrates the mechanism of action of localized delivery of clonidine and that it has analgesic and anti-inflammatory effects.

FIG. 3 illustrates the mechanism of action of localized delivery of clonidine and that it has analgesic and anti-inflammatory effects. It is also noted that clonidine has alpha-2 adrenergic receptor independent activity based in part on inhibition of the voltage-gated sodium and potassium channels.

Example 4

Figure 4:
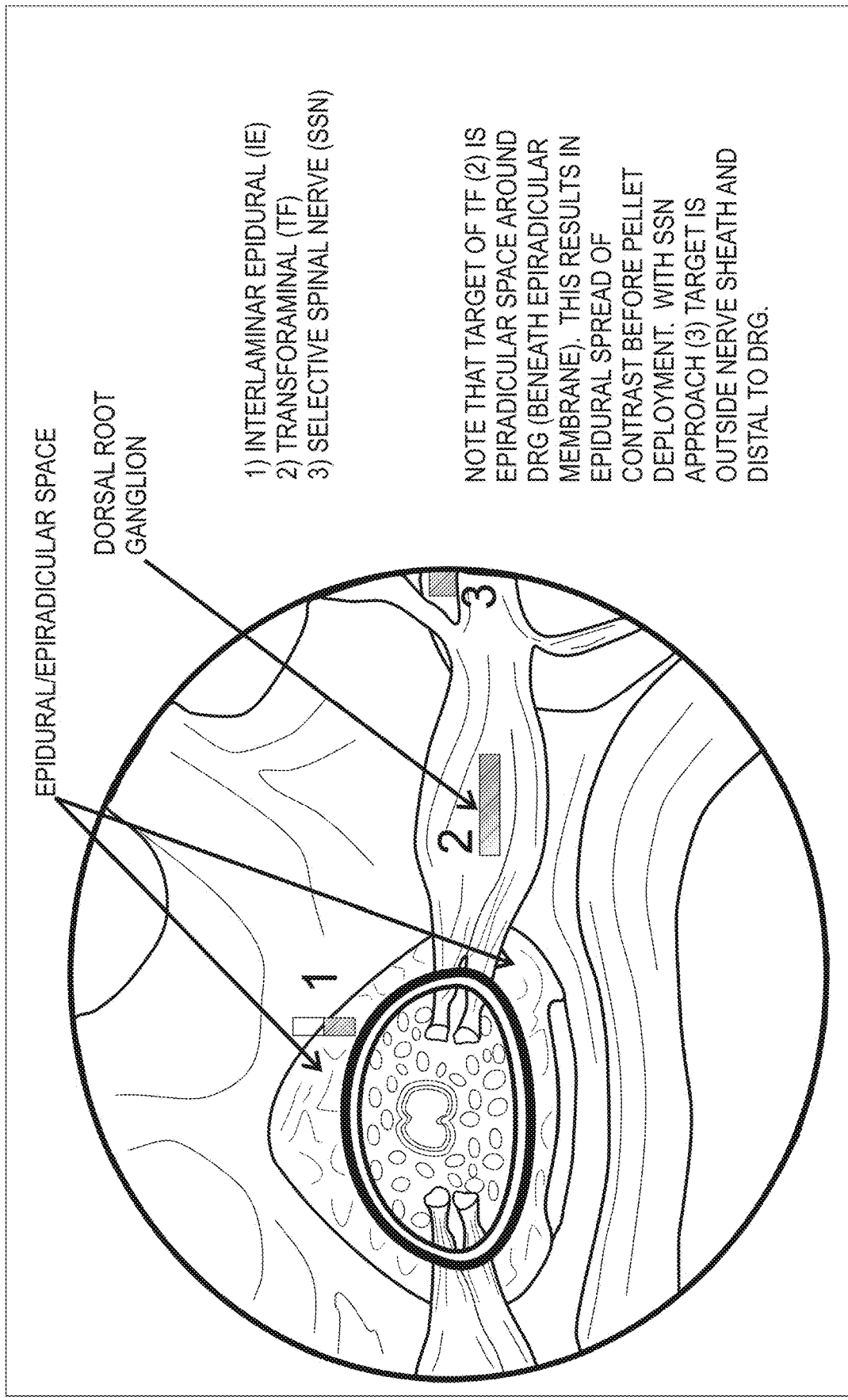
FIG. 4 illustrates areas for local delivery of clonidine depots and that there is little or no toxicity even at high doses in rat and goat studies.
Figure 5:
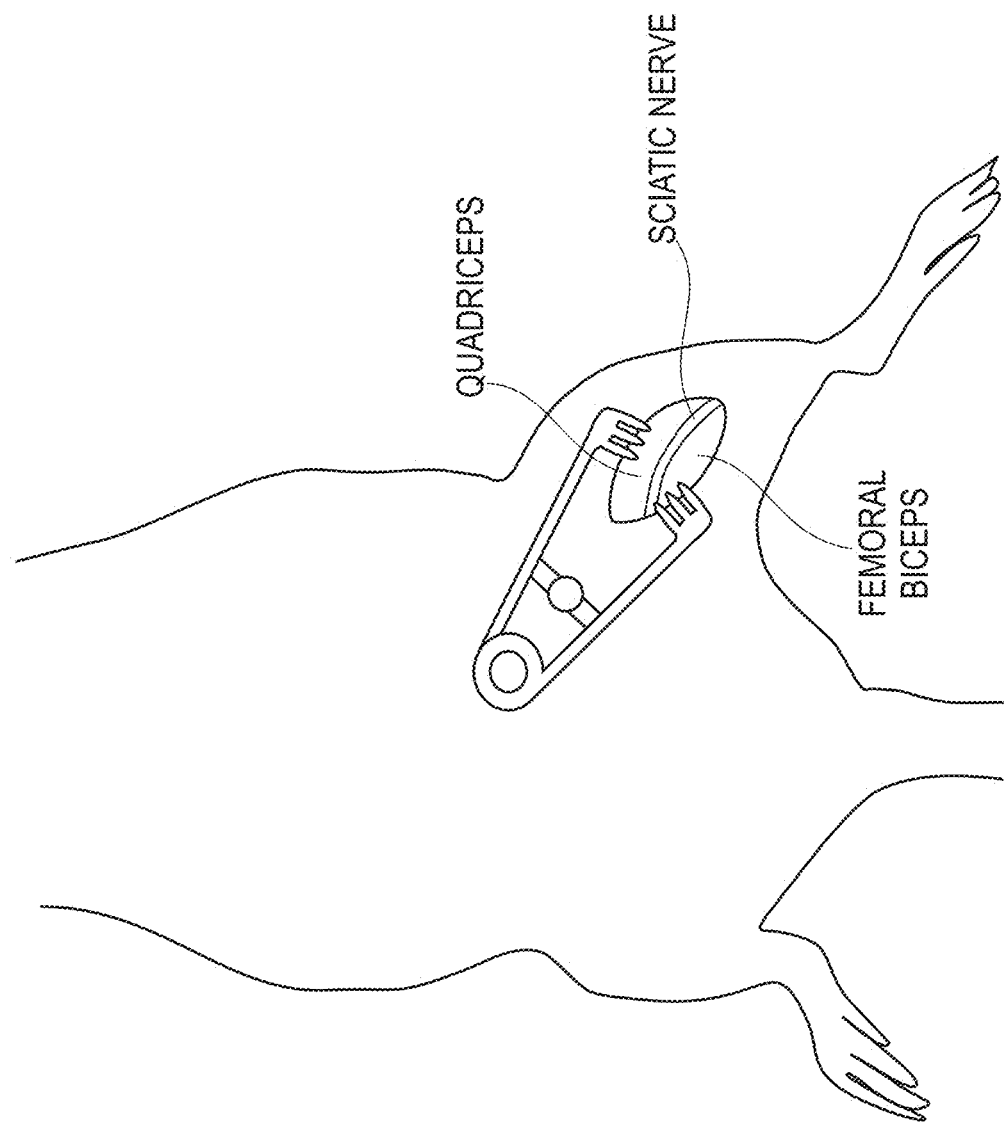
FIG. 5 illustrates areas for local delivery of clonidine depots and that there is little or no toxicity even at high doses in rat and goat studies.

FIGS. 4 and 5 illustrate areas for local delivery of clonidine depots in pellet form and that there is little or no toxicity even at high doses in rat and goat studies. The depots contained 15 wt % clonidine HCl in 85 wt % poly(D,L-lactide) and were melt extruded into a 50 µM diameter pellet. Goats had 6-18 clonidine pellets implanted using 3 approaches: an interlaminar epidural, transforaminal epidural and selective spinal nerve approaches. All approaches appear to be well tolerated and the clonidine was well tolerated. In the rat study 3-15 pellets were surgically implanted in an intermuscular pocket proximal to the sciatic nerve. There was no local tissue reaction observed. High doses of clonidine greater than 6 mg/kg in rats (which is equivalent to greater than 200 pellets in humans) exhibit systemic signs of stress during the first week.

Example 5

Figure 6:
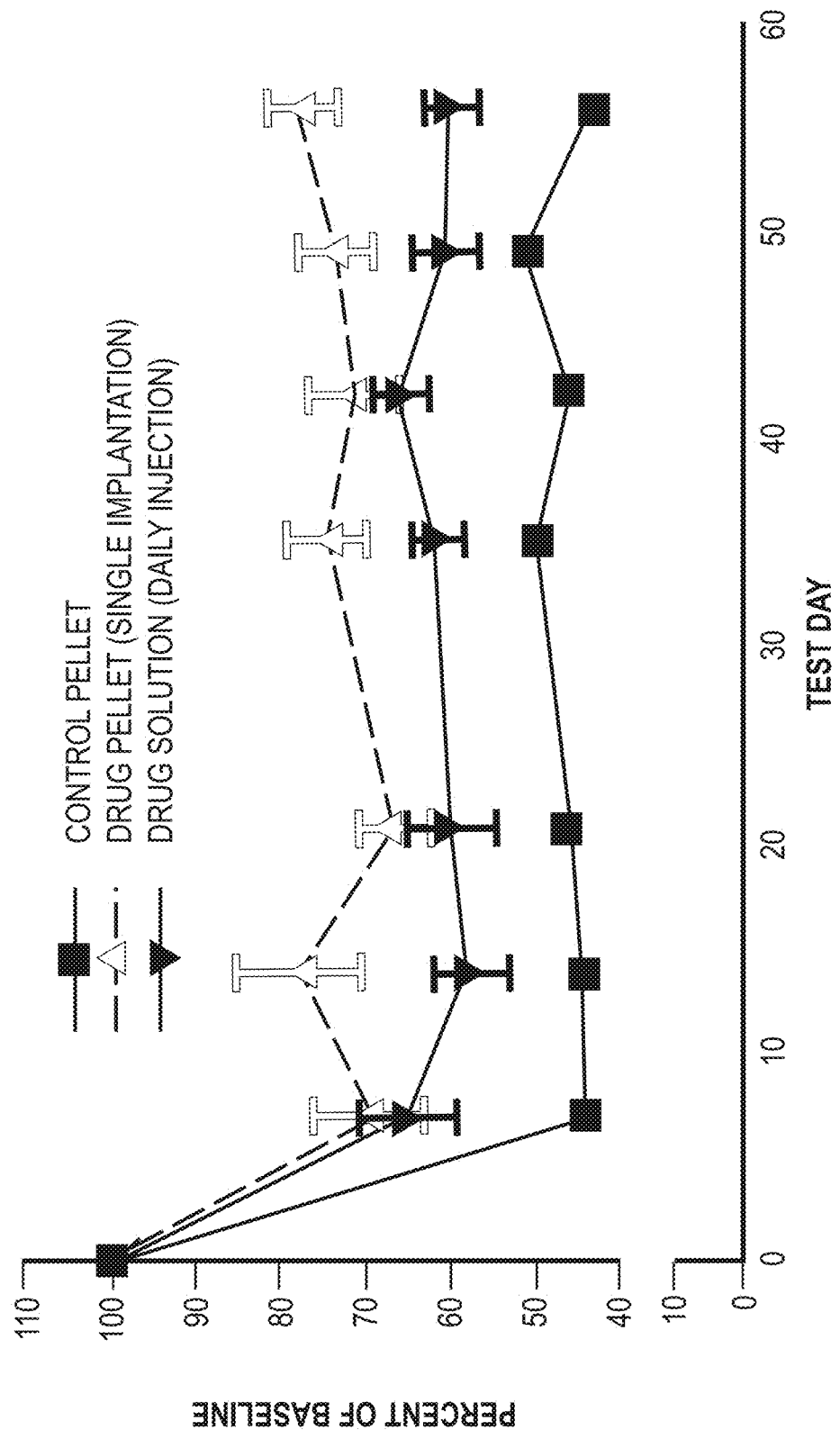
FIG. 6 illustrates efficacy of clonidine depot delivered to relieve chronic pain from an injury to the sciatic nerve in a rat model.
Figure 7:
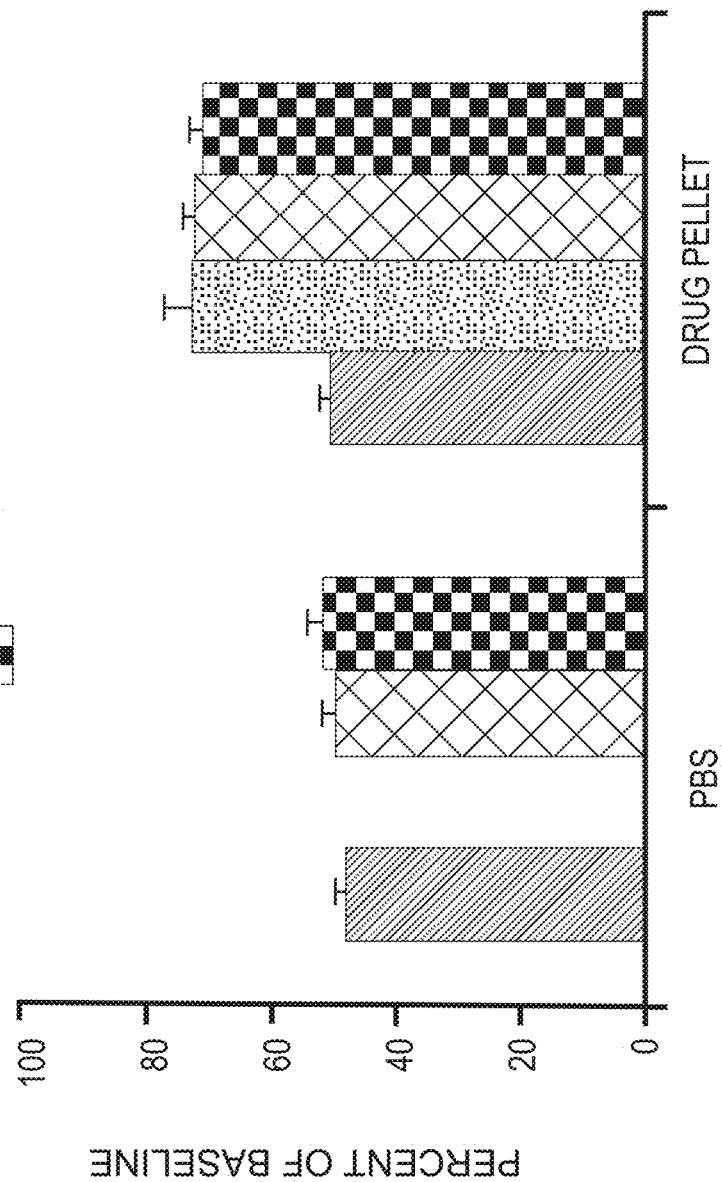
FIG. 7 illustrates efficacy of clonidine depot delivered to relieve chronic pain from an injury to the sciatic nerve in a rat model.
Figure 8:
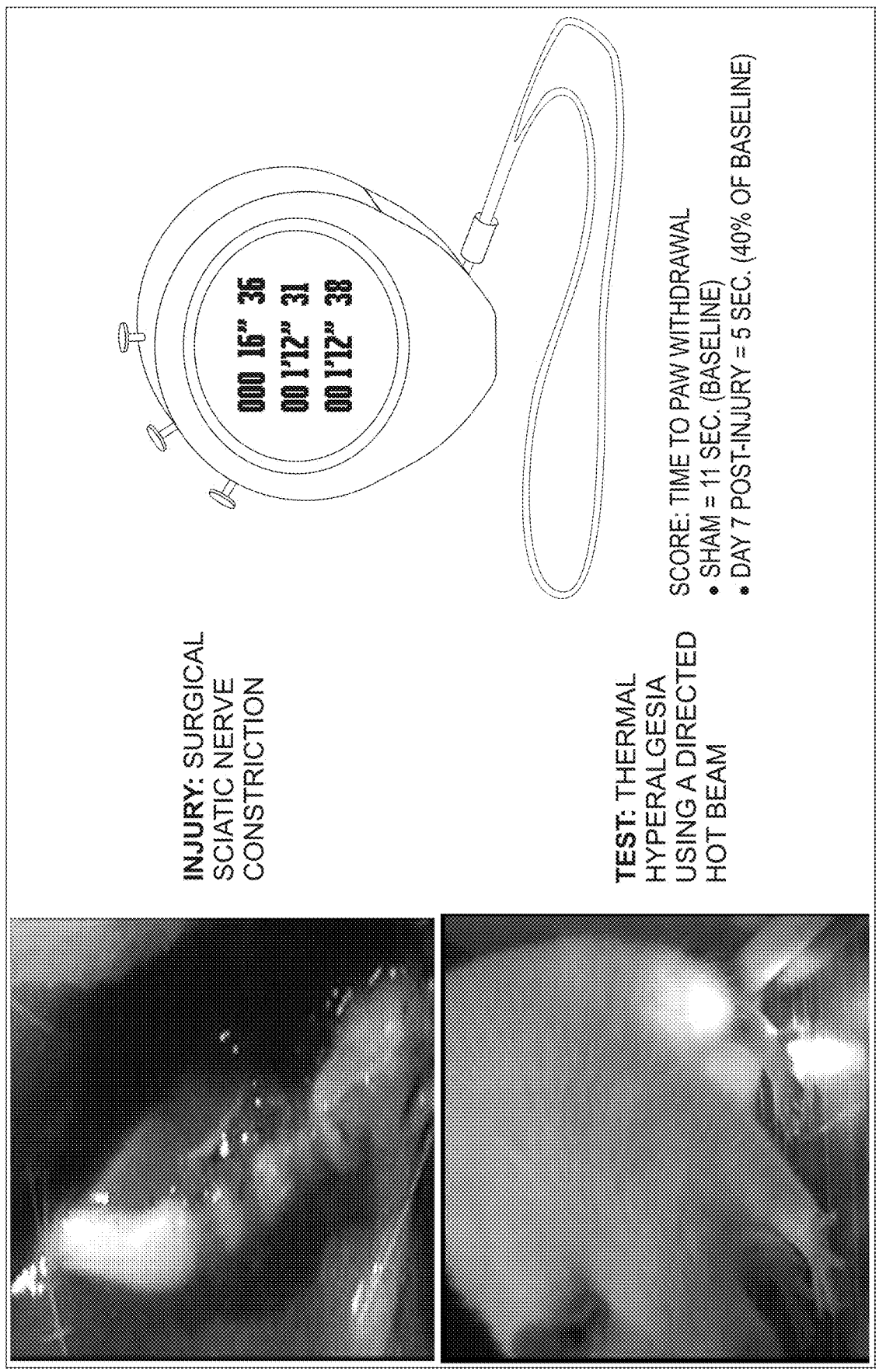
FIG. 8 illustrates efficacy of clonidine depot delivered to relieve chronic pain from an injury to the sciatic nerve in a rat model.

FIGS. 6-8 illustrate efficacy of clonidine depot pellets containing 15 wt % of clonidine in 85 wt % poly(D,L) lactide delivered to relieve chronic pain from an injury to the sciatic nerve in a rat model. There was sustained pain relief exhibited.

FIG. 6 is a graph illustrating sustained pain relief. A control depot, a clonidine drug depot in the form of a pellet containing 15 wt % of clonidine in 85 wt % poly(D,L) lactide and an injectable clonidine drug solution (20 µg/kg/day) were tested. The clonidine drug depot and the injectable clonidine drug solution exhibited sustained pain relief.

FIG. 7 is a graph illustrating that the effect of the clonidine is initiated after only a few hours post administration. The drug depot in the form of a pellet containing 15 wt % of clonidine in 85 wt % poly(D,L) lactide had the highest percent of baseline after 4 hours post administration. The drug pellet was also effective 1 day, 3 days and 7 days post administration.

FIG. 8 depicts images of the site of injury, such as, at the sciatic nerve in a rat. Thermal hyperalgesia was tested using a direct hot beam administered to the rat subject. The time to paw withdrawal score was taken. The sham equaled to 11 seconds (baseline) and day 7 post-injury equaled 5 seconds (40% of baseline).

Example 6

Figure 9:
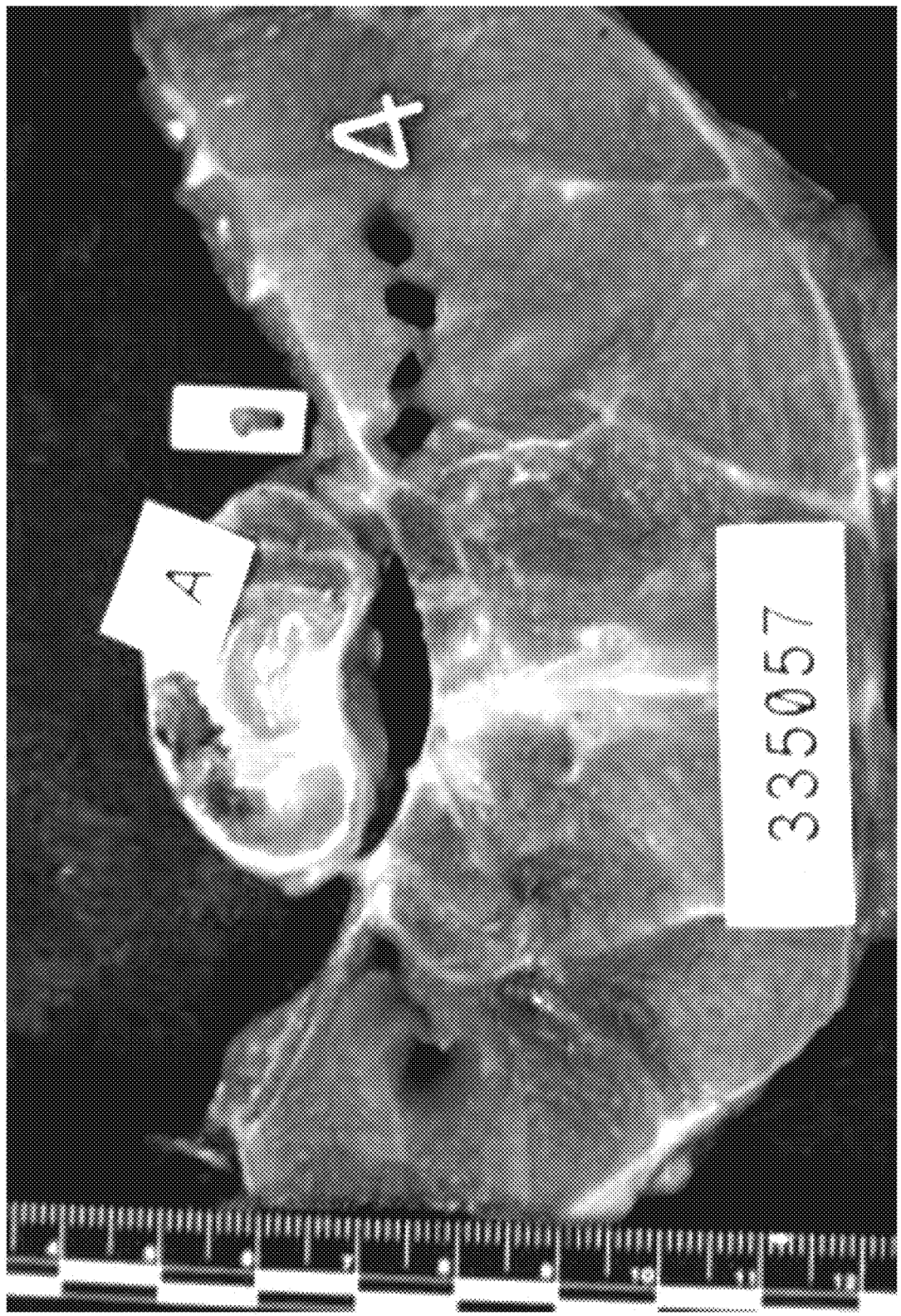
FIG. 9 illustrates rat tissue samples used in a study for tissue pharmacokinetics of clonidine from an implanted clonidine depot over a 3-month period.
Figure 10:
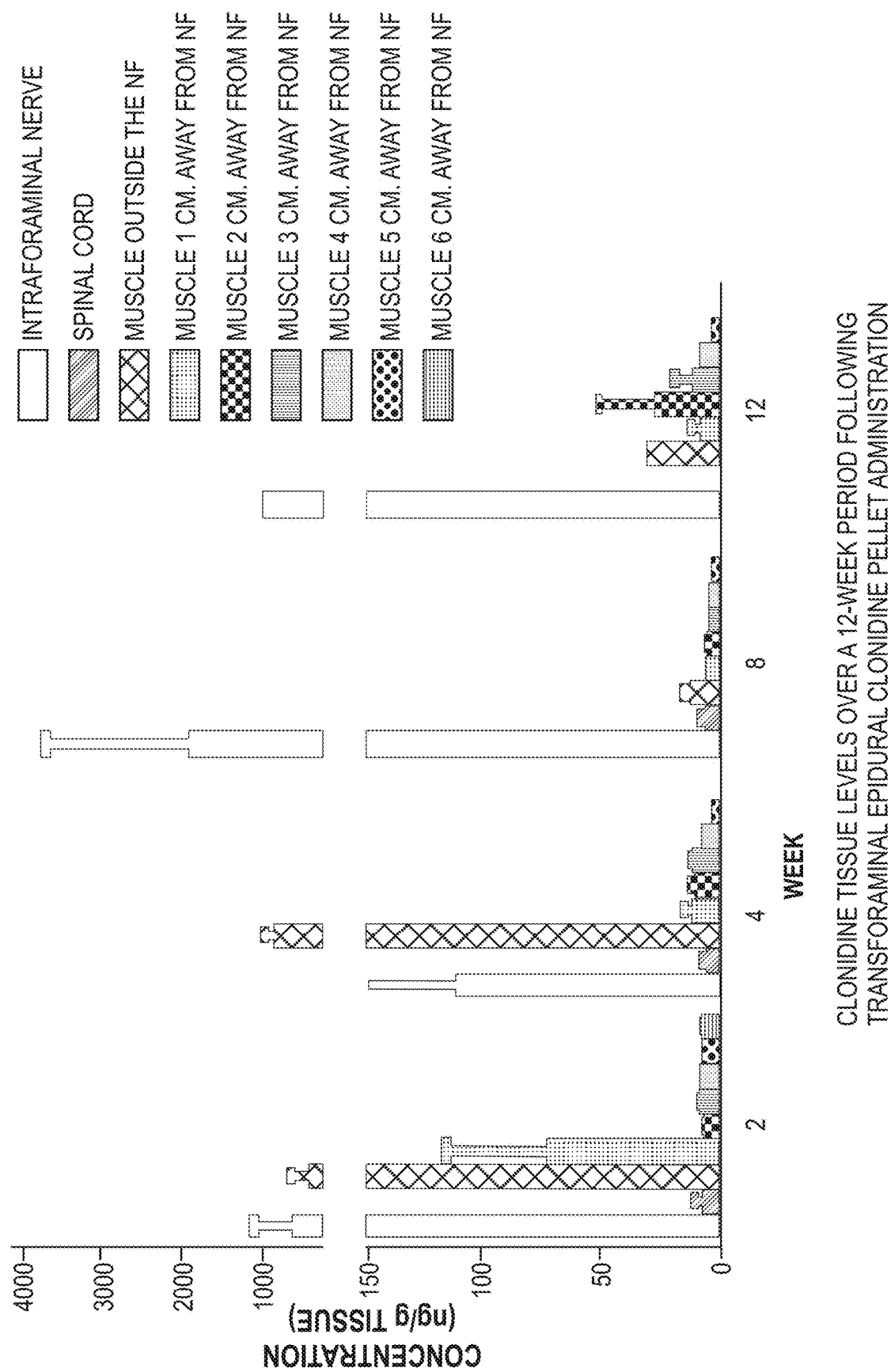
FIG. 10 illustrates tissue pharmacokinetics of clonidine from an implanted clonidine depot over a 3-month period.

FIGS. 9 and 10 illustrate tissue pharmacokinetics of clonidine from an implanted clonidine depot containing 5 wt % clonidine in 95 wt % poly(D,L) lactide over a 3-month period. There was preferential clonidine accumulation in the target spinal nerve/roots in the localized delivery of the depot. The clonidine plasma levels were below the detectable limit in the plasma, which indicates that the clonidine exerts its effects locally at the target tissue site when providing pain relief over the 3-month period. Further, systemic concentrations in human Duraclon patients are typically 2.4 ng/mL, steady state CSF concentrations 5-10 ng/mL. Skin concentrations of 10 ng/g or higher associated with analgesic effect in incisional pain model, with no temporal relationship to systemic exposure.

Concentration may need complete receptor-independent blockade of axonal transmission (true anesthetic effect) appear to be higher, with partial inhibition in clinical range. Complete blockade in vitro preparations may occur at 20 mcg/mL (or 20000 ng/mL). It should be noted that 300 mcg clonidine HCl is approximately equivalent to 1 pellet of the clinical trial formulation.

Example 7

Purpose: While clinical and non-clinical studies demonstrate a regional analgesic effect of clonidine distinct from effects on the central nervous system (CNS), the mechanism of action and precise site of action remain unclear. The purpose of this study was to test the hypothesis that clonidine has a direct effect on peripheral axons in vivo.

Methods: Peripheral nerve function was assessed by evoked action potentials (sciatic nerve) as well as spinal somatosensory evoked potentials in male Sprague Dawley (SD) rats. The tibial nerve was stimulated with 10 milliamperes (mA) constant current delivered with platinum microelectrodes placed proximal to the internal ankle. Recording electrodes were placed near the proximal sciatic nerve at the sciatic notch (ipsilateral and contralateral nerves) and over the L5 interlaminar space. Measurements were obtained with a Biopac MP36 amplifier and data acquisition unit (Biopac Systems, Goleta, Cal). Following collection of baseline data, test solutions were administered directly into the subparaneural compartment of the right sciatic nerve, approximately 0.5 cm proximal to the tibial/fibular bifurcation, using a Hamilton HPLC injection syringe (20 µl, injection volume). Saline served as the negative control and commercial 2% lidocaine for injection served as the positive control. Clonidine was administered at escalating doses including 50, 100, 200, and 500 µg (minimum n=3 per dose).

Figure 12:
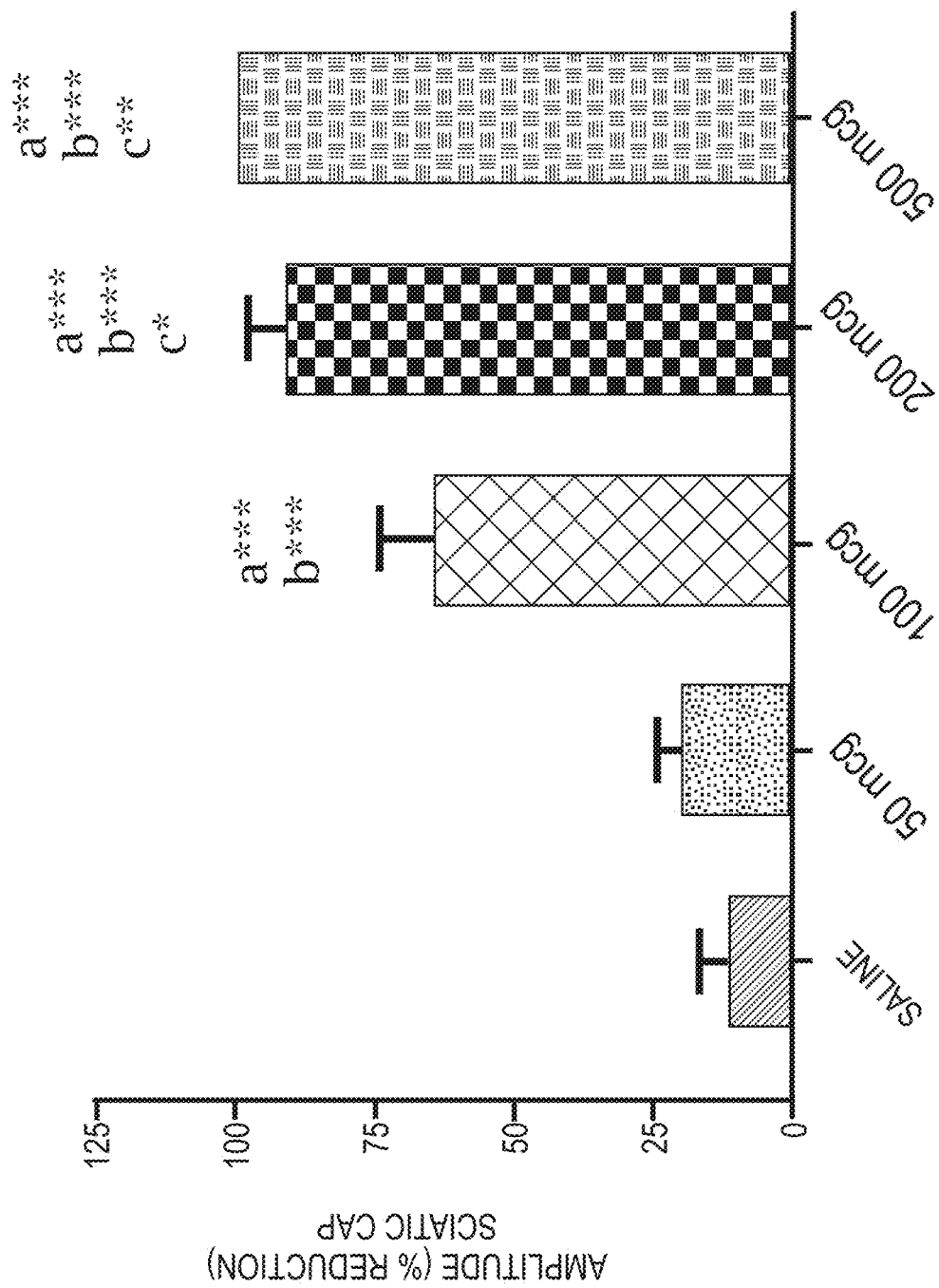
FIG. 12 shows reduction in sciatic CAP amplitude (Spinal). Amplitude percentage reduction of sciatic CAP was compared when administering saline, clonidine at various doses and yohimbine.
Figure 13:
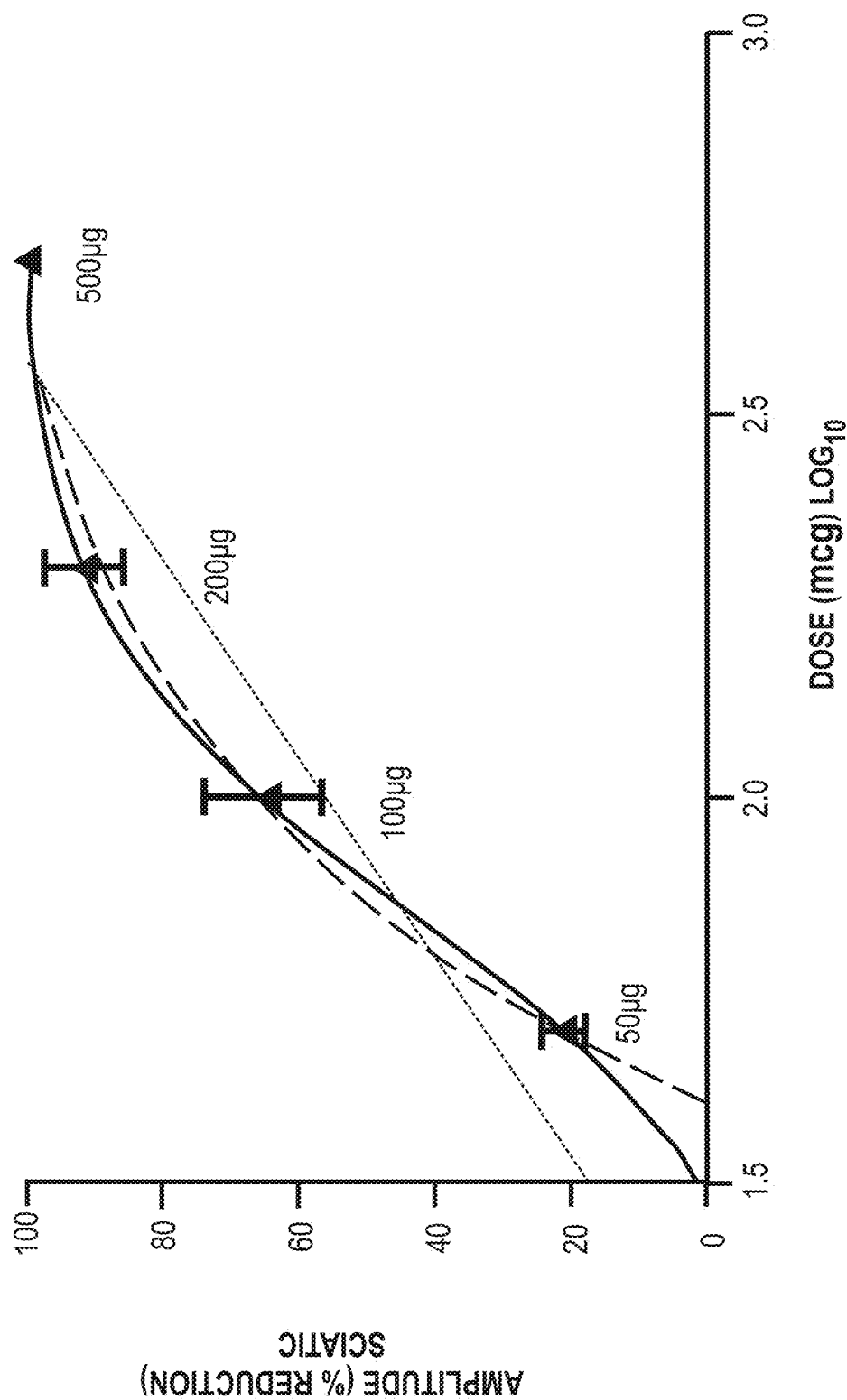
FIG. 13 shows characterization of dose-response relationship (Sciatic CAP). Amplitude percentage reduction of sciatic CAP was compared when administering saline, clonidine at various doses and yohimbine.
Figure 14:
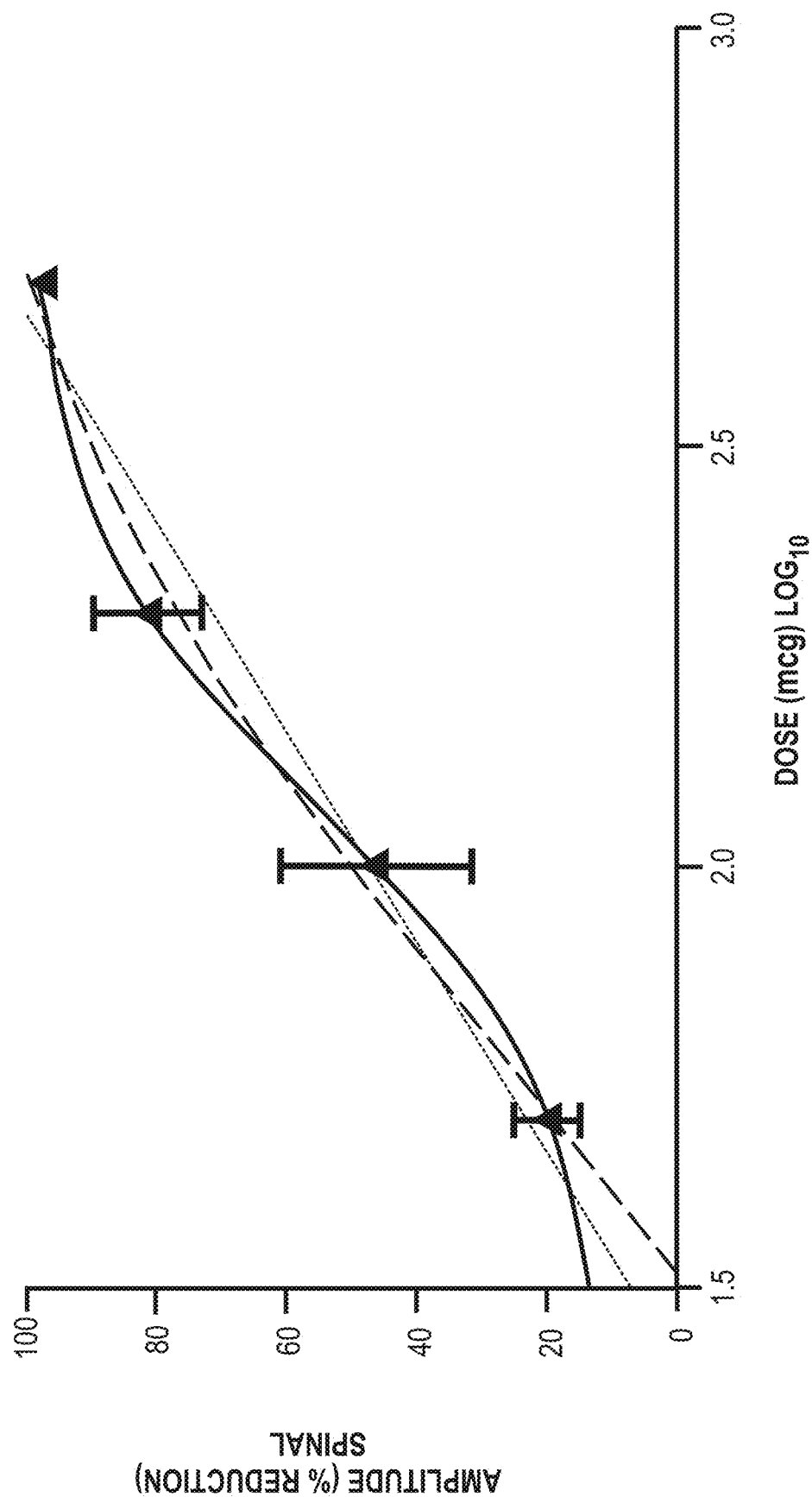
FIG. 14 illustrates characterization of dose-response relationship (SSEP). Amplitude percentage reduction of SSEP was compared when administering saline, clonidine at various doses and yohimbine.
Figure 15:
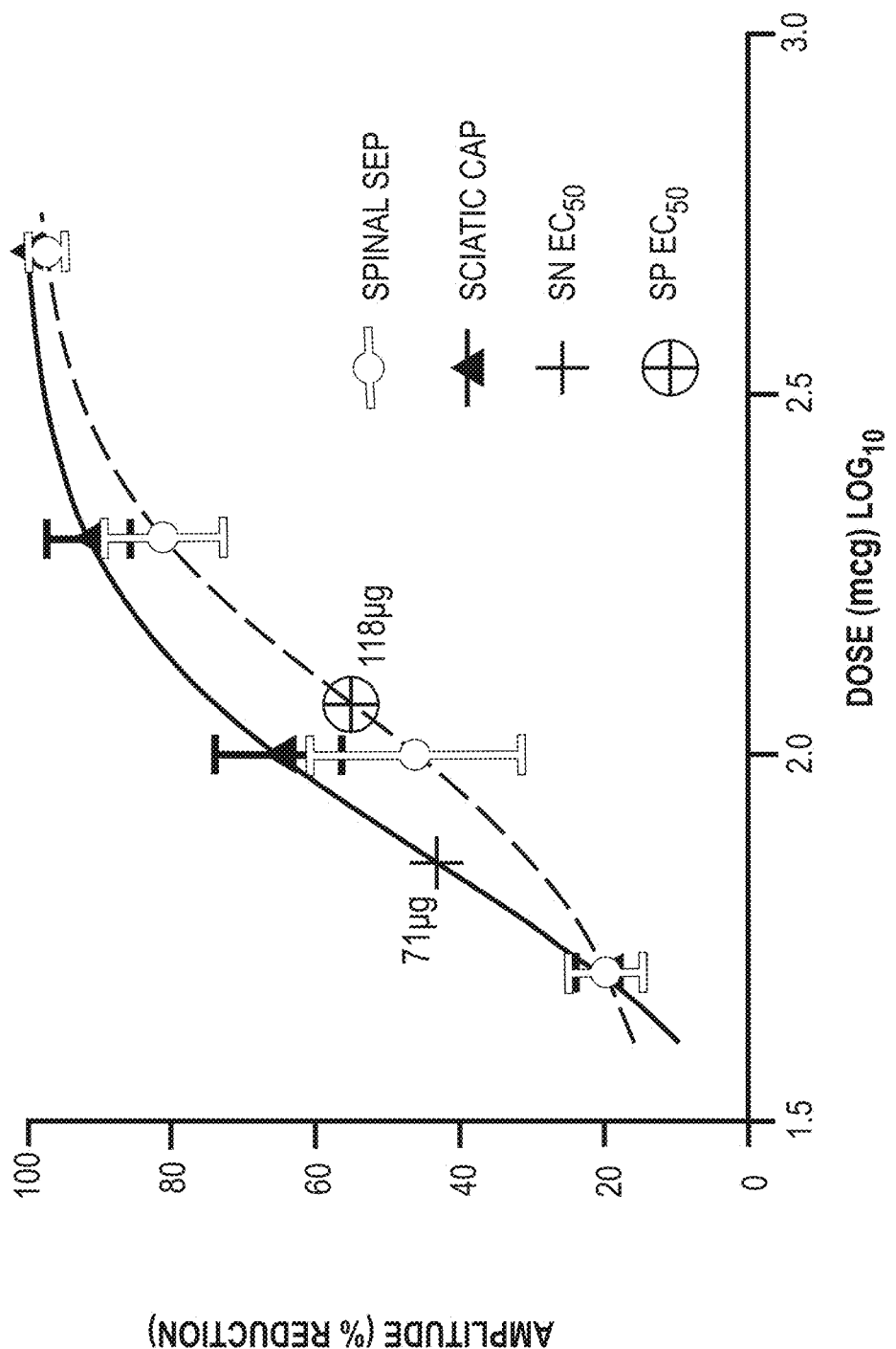
FIG. 15 illustrates amplitude reduction depending on the clonidine dose administered.

Results: As expected, lidocaine eliminated compound action potentials recorded in the ipsilateral sciatic nerve and spine for >20 minutes but did not affect the contralateral sciatic nerve. There was a clear dose-response relationship of clonidine, with a significant reduction in action potential amplitude versus control in animals treated with the 100 µg dose, and a significantly greater reduction in amplitude in animals treated with the 200 µg dose. The 500 µg dose eliminated spinal somatosensory evoked potentials in 3 out of 4 animals (FIG. 11) and eliminated compound action potentials in the ipsilateral sciatic nerve in all cases (FIG. 12). The contralateral sciatic nerve was not affected by any dose of clonidine (including spinal recordings following contralateral stimulation), suggesting that systemic distribution to the CNS does not contribute to the observed regional effect. In a separate set of experiments, 1 mg of yohimbine HCL, a potent α2AR antagonist, was injected SQ (1 mL volume) 5 minutes prior to intraneural delivery of the highest test dose of clonidine (500 µg). The elimination of evoked action potentials was unaffected, suggesting that this effect is entirely receptor independent. Since peripheral axons are not believed to contain membrane receptors, including α2AR, this finding is consistent with the hypothesis that clonidine has a direct effect on peripheral axons themselves (as opposed to distribution to nerve endings). The dose-response relationship is best described by the sigmoidal, 4 parameter non-linear regression (e.g., Hill equation) typical of ligand binding to an endogenous macromolecule (FIGS. 13 and 14). The $EC_{50}$ was 71 µg for evoked compound action potentials in the sciatic nerve and 118 µg for spinal somatosensory evoked potentials (FIG. 15). The most plausible target of clonidine is the voltage gated $Na^+$ channels involved in propagating action potentials through sensory fibers to the CNS, although an unidentified intermediate target cannot be excluded.

Conclusion: This study suggests that intraneural depots of clonidine and similar imidazoline compounds may be viable alternatives to cytotoxic (including neurotoxic) amide anesthetics.

Figure 11:
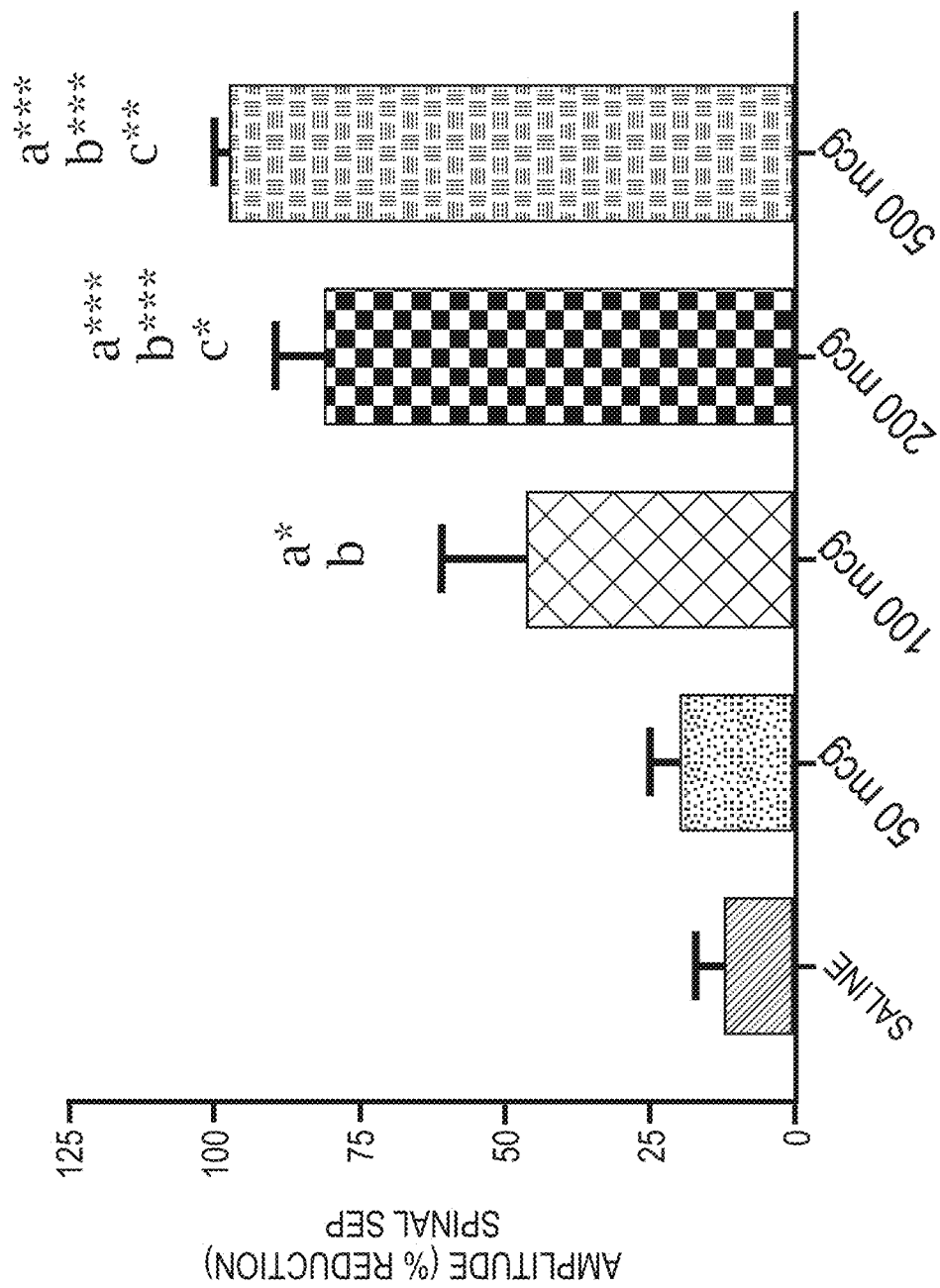
FIG. 11 illustrates a reduction in SEP amplitude (Spinal). Amplitude percentage reduction of spinal SEP was compared when administering saline, clonidine at various doses and yohimbine.

FIG. 11 illustrates a reduction in SEP amplitude (Spinal). Data was analyzed by ANOVA (F=22.04, p<0.001) followed by Fisher Fisher's LSD, making all possible pairwise comparisons. The symbol a represents p<0.05 for pairwise comparison to saline control; the symbol b represents p<0.05 pairwise comparison to 50 µg; the symbol c represents p<0.05 pairwise comparison to 100 The superscripts indicate p<0.01 (α=0.05): *p<0.01; p<0.001; *p<0.0001. It should be noted that pre-administration of 1 mg of yohimbine (α2 AR antagonist) prior to intraneural injection of the $EC_{max}$ (500 µg) had had no effect (action potential eliminated in all cases, not shown).

FIG. 12 shows reduction in sciatic CAP amplitude (Spinal). Data was analyzed by ANOVA (F=56.97, p=0.0001) followed by Fisher Fisher's LSD, making all possible pairwise comparisons. The symbol a represents p<0.05 for pairwise comparison to saline control; the symbol b represents p<0.05 pairwise comparison to 50 µg; the symbol c represents p<0.05 pairwise comparison to 100 The superscripts indicate p<0.01 (a=0.05); *p<0.01; p<0.001; *p<0.0001. It should be noted that pre-administration of 1 mg of yohimbine (α2 AR antagonist) prior to intraneural injection of the $EC_{max}$ (500 µg) had had no effect (action potential eliminated in all cases, not shown).

FIG. 13 shows characterization of dose-response relationship (Sciatic CAP). Doses were converted to $\log_{10}$, with percent reduction in amplitude from the baseline treated as a response. Data was analyzed by linear regression, simple non-linear regression, and four parameter non-linear regression, assuming the inflection point at approximately $EC_{50}$ (e.g., Hill's constant). Goodness of fit ($R^2$) values were 0.7993, 0.9106, and 0.9141 for linear regression, 3PL non-linear regression, and 4PL non-linear regression, respectively. Note that a single outlier test was removed from the 50 µg treatment group.

FIG. 14 illustrates characterization of dose-response relationship (SSEP). Doses were converted to $\log_{10}$, with percent reduction in amplitude from the baseline treated as a response. Data was analyzed by linear regression, simple non-linear regression, and four parameter non-linear regression, assuming an inflection point at approximately $EC_{50}$ (e.g., Hill's constant). Goodness of fit ($R^2$) values were 0.7626, 0.7845, and 0.7932 for linear regression, 3PL non-linear regression, and 4PL nonlinear regression, respectively. It should be noted that a single outlier was removed from 50 µg treatment group.

FIG. 15 illustrates amplitude reduction depending on the clonidine dose administered. The comparison of dose-response relationship for sciatic CAPs recordings are represented by the black line and spinal somatosensory EPs are represented by the dashed line. For parameter (sigmoidal) non-linear regression was selected based on trend of superior fit for both endpoints (compared to linear or standard non-linear regression). Hill's coefficients were 2.507 and 2.326 for SSEP and Sciatic CAP, respectively. Goodness of fit ($R^2$) was 0.7832 for SSEP equation and 0.9141 for Sciatic CAP equation. Although the spinal equation appears to be shifted slightly to the right of the sciatic equation, no differences between curves approached statistical significance. The sigmoidal dose-response relationships are typical of ligand binding to a biochemical macromolecule, suggesting that clonidine interacts with a specific membrane component of axon(s). We hypothesize this to be voltage-gated ion channels.

Figure 16:
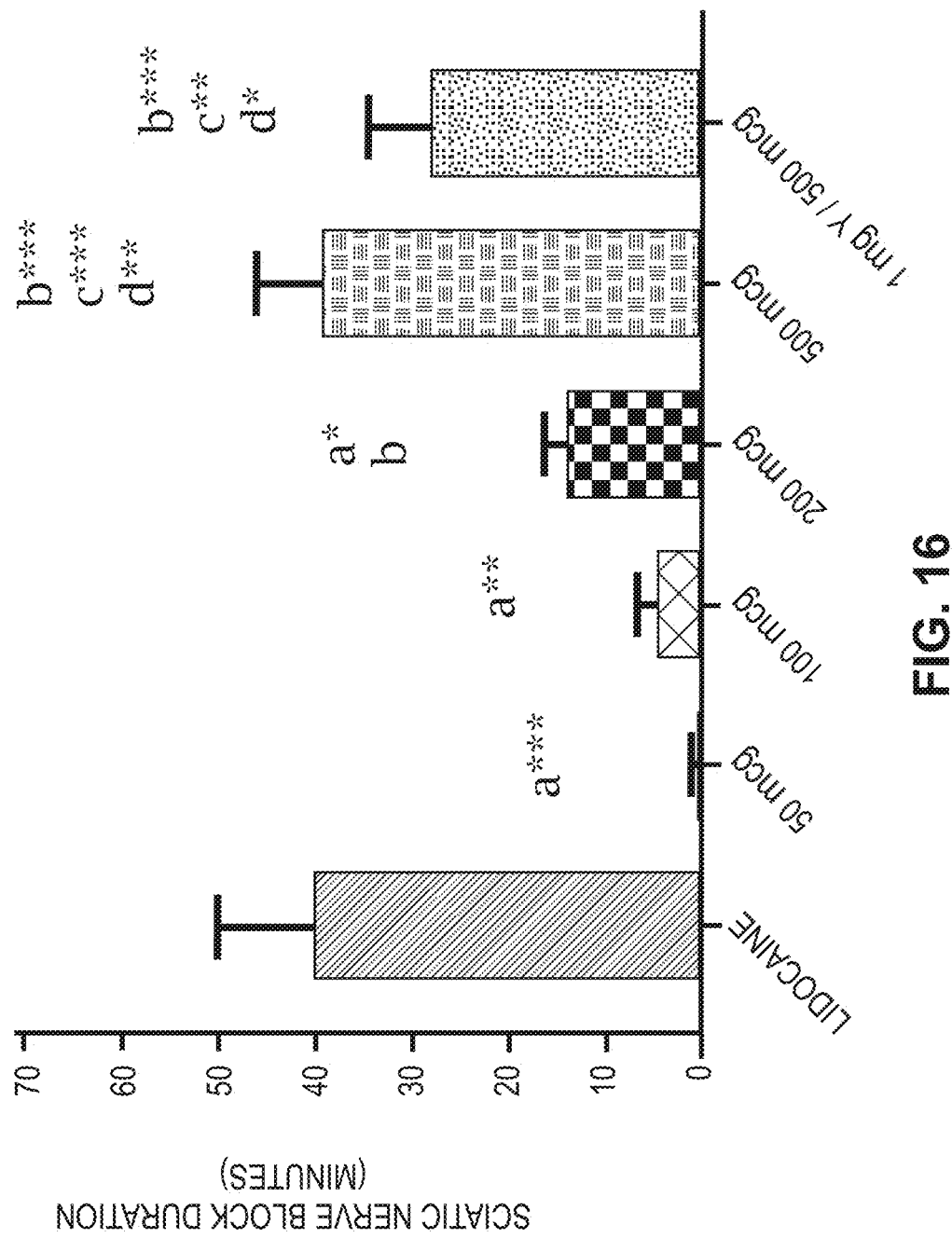
FIG. 16 illustrates sciatic nerve block duration when lidocaine, clonidine and yohimbine are administered to a site of treatment.

FIG. 16 illustrates sciatic nerve block duration when lidocaine, clonidine and yohimbine are administered to a site of treatment. The sciatic nerve block duration was assessed by time until induced action potential amplitude exceeded 50% of the baseline. Data was analyzed by ANOVA (F=15.4, p<0.0001) followed by Fisher Fisher's LSD, making all possible pairwise comparisons. Symbol a represents p<0.05 for pairwise comparison to the lidocaine control; symbol b represents p<0.05 pairwise comparison to 50 µg; symbol c represents p<0.05 pairwise comparison to 100 µg; and symbol d represents p<0.05 pairwise comparison to 200 µg. The superscripts indicate p<0.01 (α=0.05): *p<0.01; p<0.001, and *p<0.0001. It should be noted that the saline control did not cause induced potentials to drop below the 50% threshold. Since pre-administration (t=(−)10 minutes) of the α2 adrenergic antagonist yohimbine did not inhibit the subsequent effect of clonidine, the anesthetic-like effect appears to be receptor-independent.

It was concluded that clonidine and related imidazoline compounds have anesthetic-like and concentration dependent effects on nerve fibers. While general anesthetic or regional co-anesthetic effects of imidazoline compounds has been previously reported, such effects have generally been assumed to be receptor-dependent. The receptor-independent effect demonstrated in proof-of-concept data allows for a direct effect on peripheral axons, such that targeted delivery would not allow for diffusion to peripheral nerve endings or central synapses. Given that the receptor-independent effects appear to take place at higher concentrations than receptor dependent effects, and given that the accepted systemic off target effects associated with these compounds are receptor dependent, a technology designed to concentrate these compounds around a sensory axon bundle innervating a painful region would leverage this novel mechanism for the treatment of acute pain. In some embodiments, this depot configuration is designed for sub-epineural administration and to limit systemic absorption, with maximal retention of drug at the indication-specific site of action.

Figure 17:
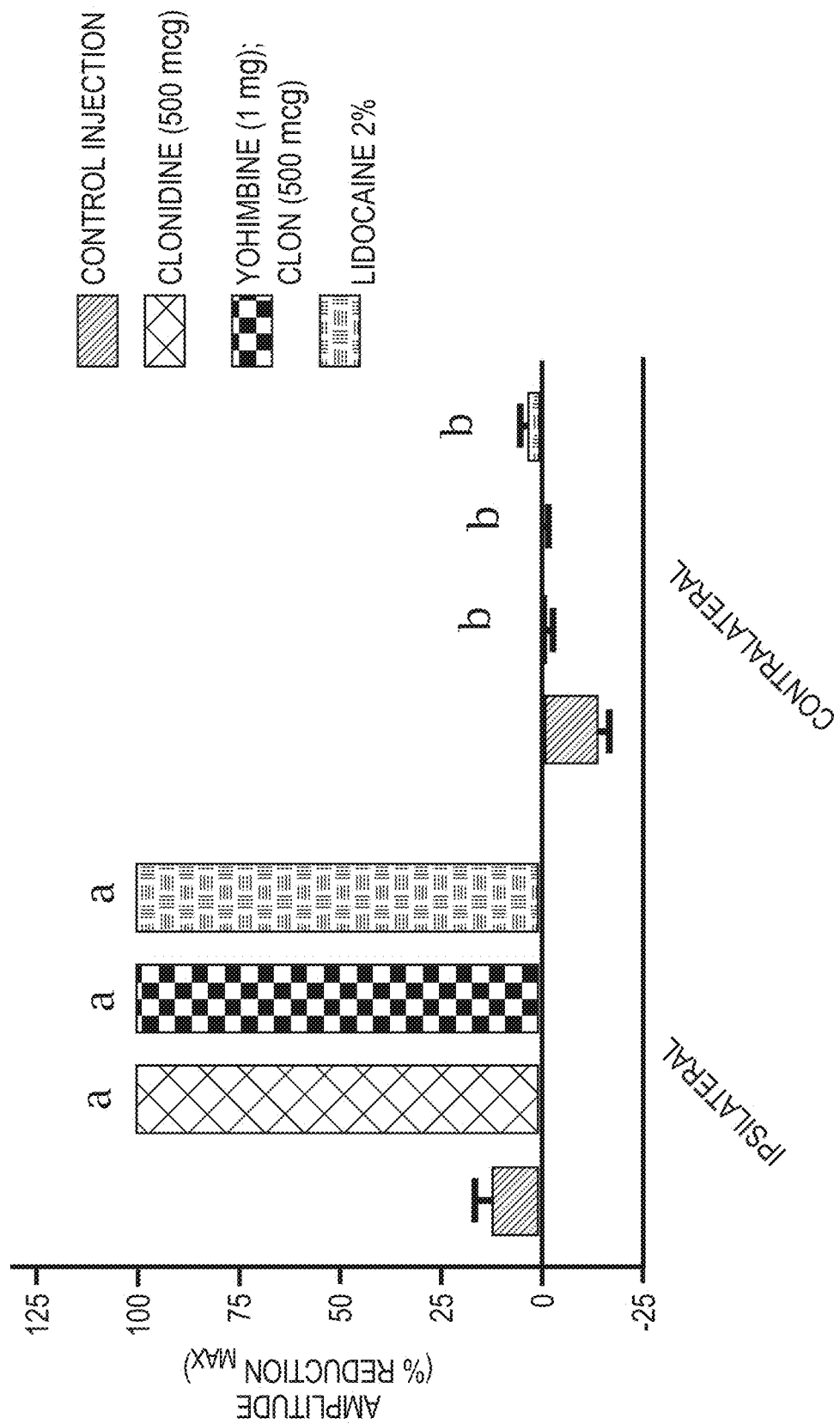
FIG. 17 illustrates the reduction in evoked sciatic nerve action potential amplitude, expressed as maximum percentage reduction versus baseline ($T_o$) when a saline control, clonidine at various doses, yohimbine and lidocaine are administered ipsilaterally and contralaterally to a site of treatment.

FIG. 17 shows the reduction in evoked sciatic nerve action potential amplitude, expressed as maximum percentage reduction versus baseline ($T_o$). Data was analyzed by a 2-Factor ANOVA followed by Fisher's LSD post hoc, which compared each treatment to the saline control. Treatment (F=142.6, p<0.0001) and nerve (e.g., ipsilateral versus contralateral) (F=1105, p<0.0001) main effects were statistically significant, as was the interaction between main effects (F=74.6, p<0.0001). This suggests that the effect of intraneural injection is both local and receptor-independent. Symbol a represents p<0.0001 for pairwise comparison to the control injection, ipsilateral sciatic nerve; and symbol b represents p<0.01 pairwise comparison to the control, contralateral nerve. It should be noted that negative values represent an increase in action potential amplitude over the baseline. Effects on the contralateral nerve are not considered clinically significant.

Figure 18:
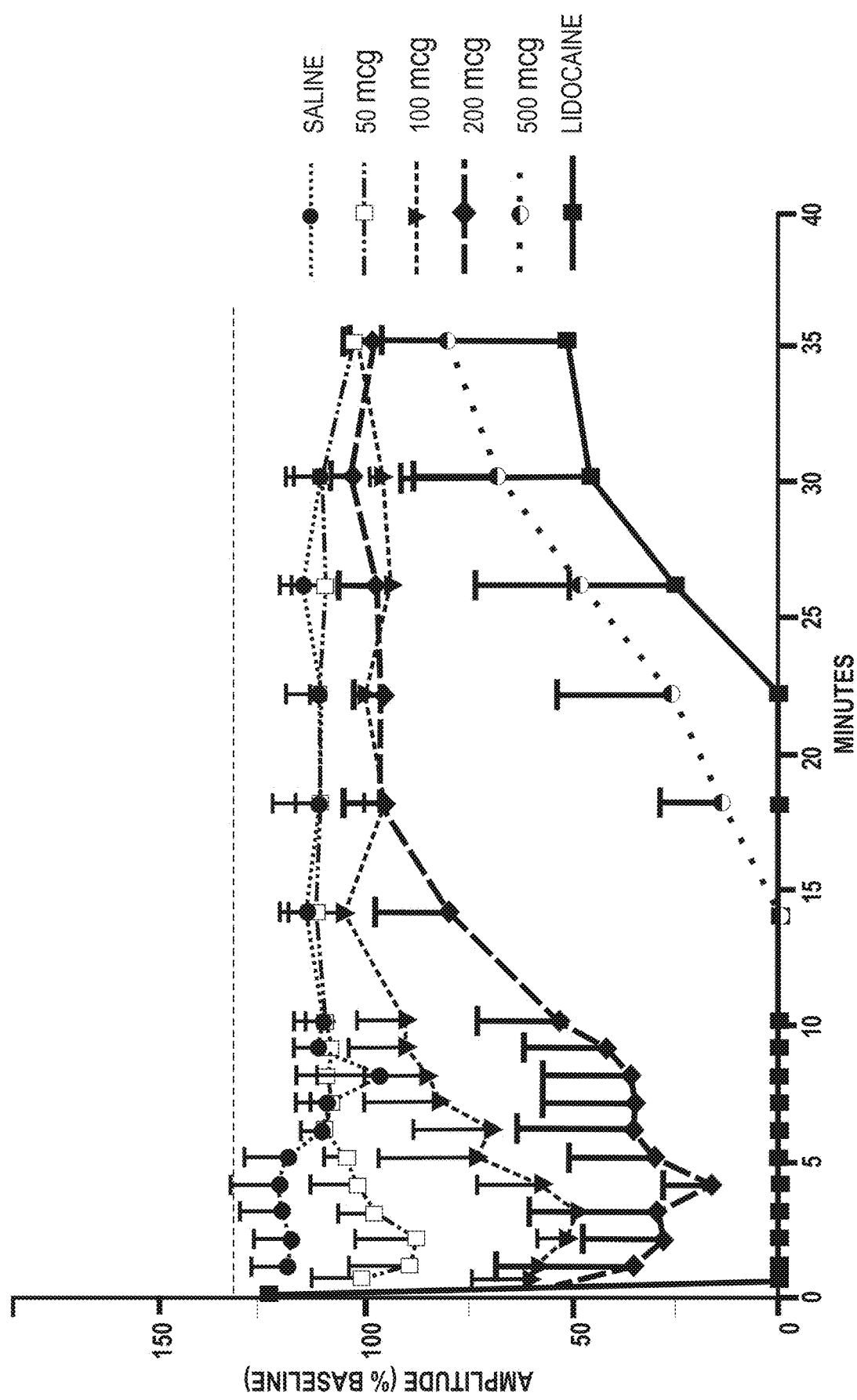
FIG. 18 illustrates sciatic evoked potential amplitude as percent of baseline over time post-injection (to time of injection) when a saline control, clonidine at various doses, and lidocaine are injected.

FIG. 18 shows sciatic evoked potential amplitude as percent of baseline over time post-injection ($T_o$ time of injection). The error bars represent mean+SEM (unidirectional error bars are used to facilitate visualization of each treatment group).

Figure 19:
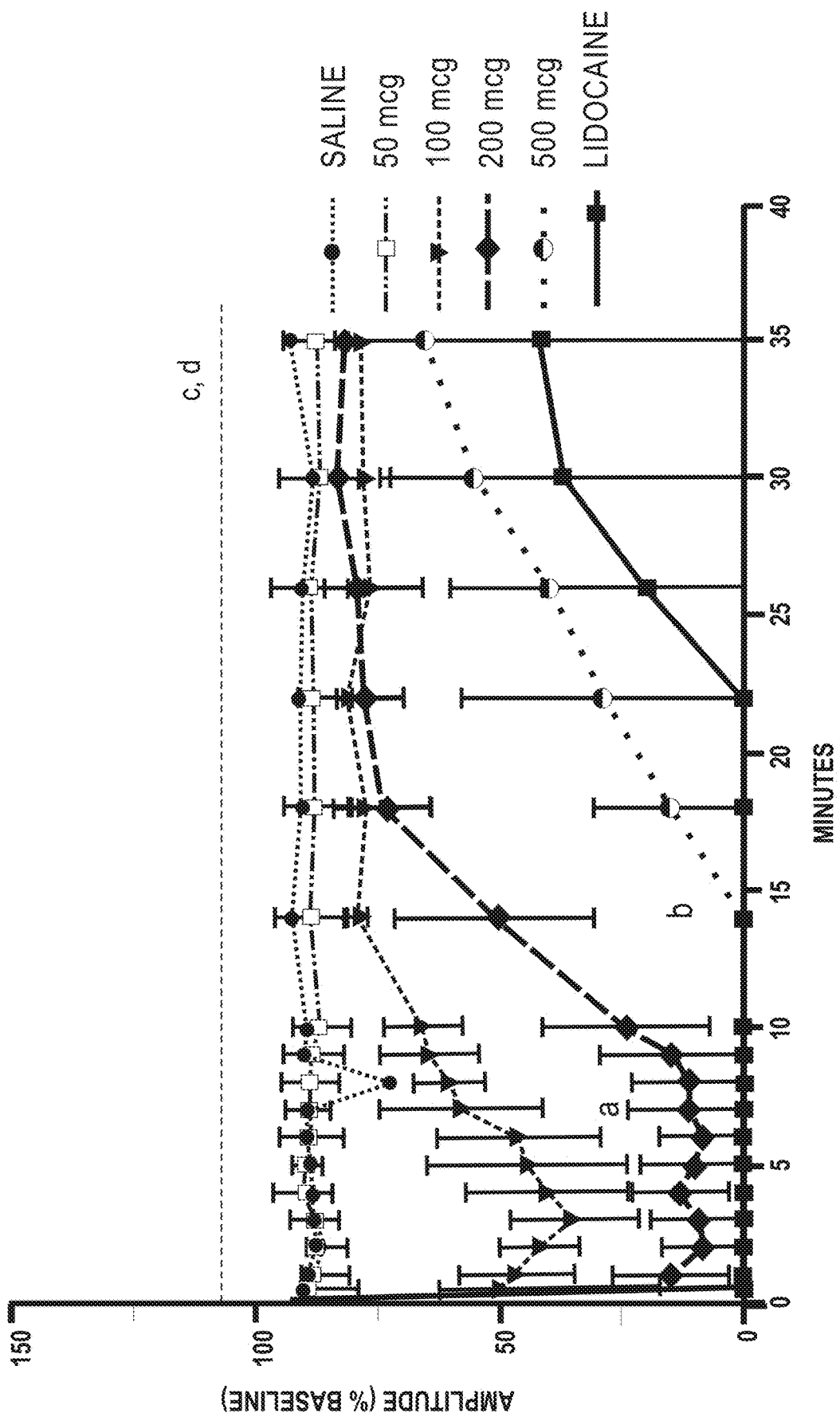
FIG. 19 illustrates sciatic evoked potential amplitude as percent of baseline over time post-injection when a saline control, clonidine at various doses, and lidocaine are injected.

FIG. 19 illustrates sciatic evoked potential amplitude as percent of baseline over time post-injection (replicates with complete data sets only, allowing for repeated measures analysis). Error bars represent mean±SEM. Treatment (F=25.27, p<0.0001) and time (F=37.69, p<0.0001) main effects were statistically significant, as was the interaction between main effects (F=5.21, p<0.0001). Symbol a represents p<0.05 for pairwise comparison between 100 µg and control through 7 minutes; symbol b represents p<0.05 pairwise comparison between 200 µg and control through 18 minutes; symbol c represents all pairwise comparisons between 500 µg clonidine and control were significant (p<0.05) through 35 minutes; and symbol d represents that all pairwise comparisons between lidocaine and control were significant (p<0.05) through 35 minutes.

Figure 20:
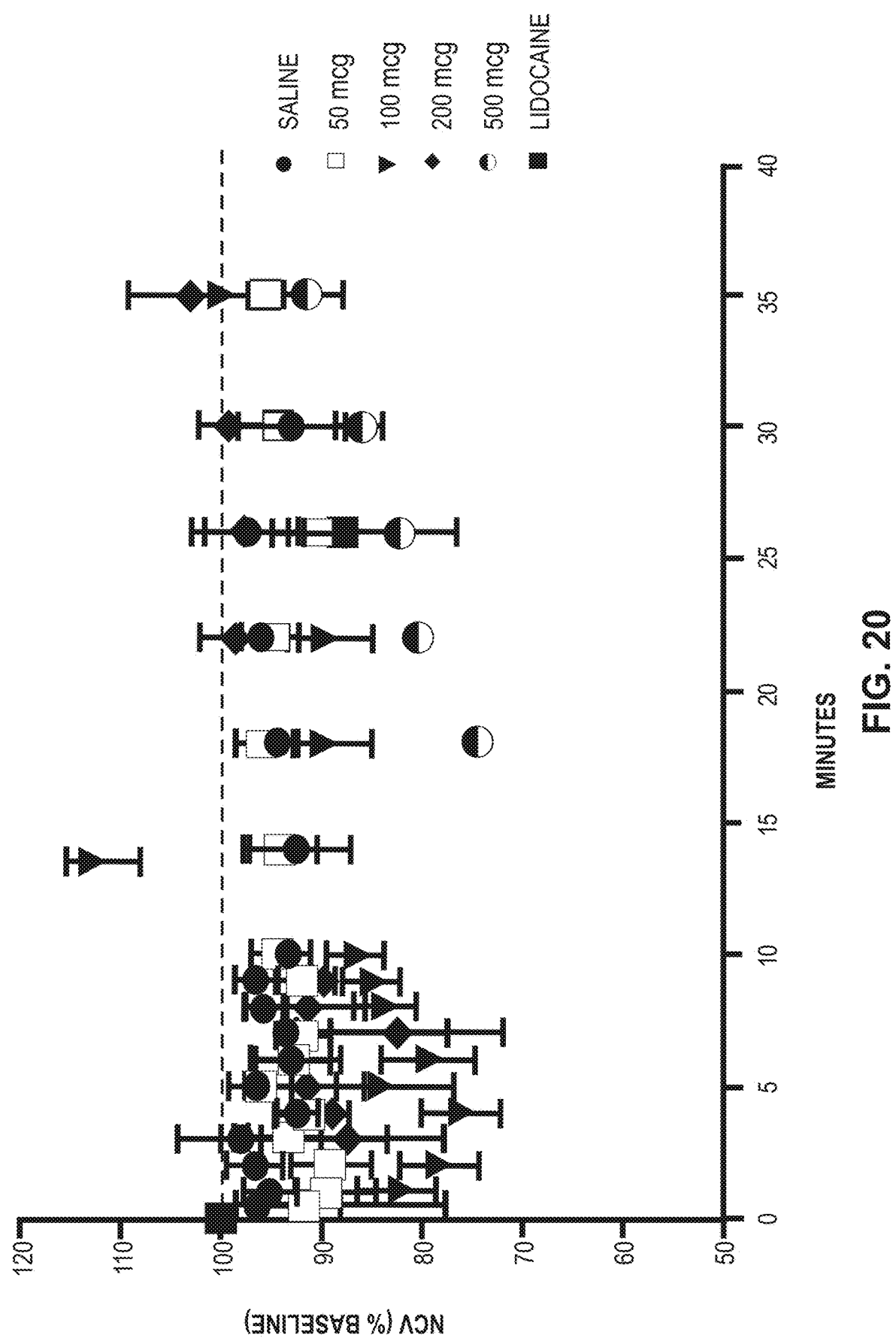
FIG. 20 illustrates the effect that saline, clonidine and lidocaine have on nerve conduction velocity (ipsilateral sciatic nerve) for a period of time (minutes).

FIG. 20 illustrates the effect that saline, clonidine and lidocaine have on nerve conduction velocity (ipsilateral sciatic nerve) for a period of time (minutes). Instances of absent evoked potential are treated as missing data (e.g., not plotted as zero velocity). The superscript indicates *p<0.05 for difference between 100 µg and control through 7 minutes. For the 500 µg clonidine and 2% lidocaine groups, comparison to control upon recovery was not possible due to inadequate replicates with detectable action potential. This data suggests that the effect of clonidine on conduction velocity is modest in fibers that continue to propagate action potentials (lower doses), and that conduction velocity is approximately normal as nerve fibers return to function (higher doses). This also appears to be true of lidocaine.

Figure 21:
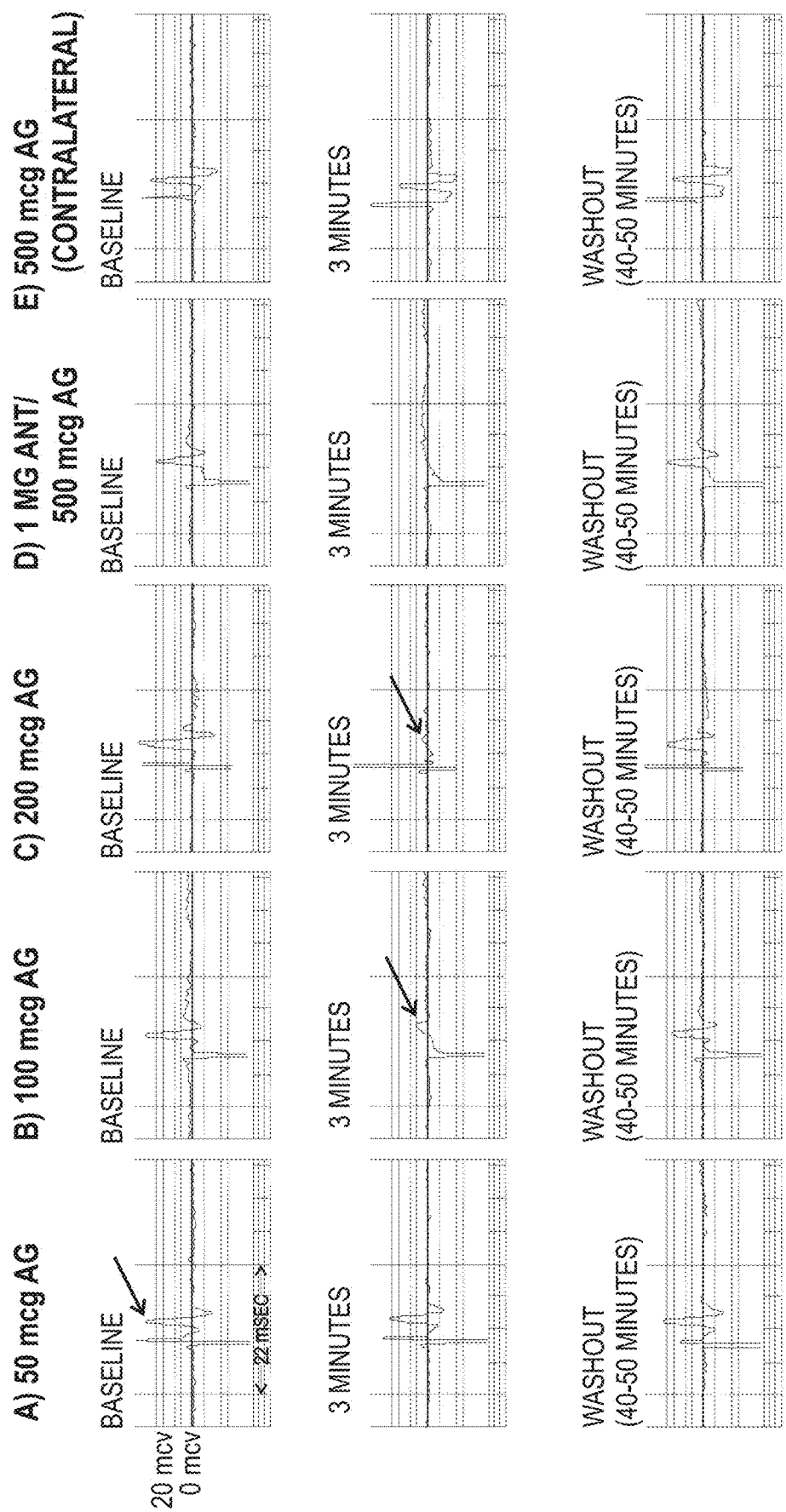
FIG. 21 depicts representative compound action potential traces (CAP), sciatic nerve. The graphs in column a) depict 50 μg of clonidine HCL which had no discernable effect on CAP amplitude. The graphs in column b) depict 100 μg of clonidine which significantly blunted CAP amplitude at 3 minutes. The graphs in column c) depict 200 μg clonidine HCL which virtually eliminated the CAP. The clonidine at 500 μg also reliably eliminated acute evoked CAPs (data not shown). The graphs in column d) depict pre-administration of 1 mg of the potent α2 adrenergic receptor antagonist yohimbine HCL which had no effect on the acute anesthetic-like action of 500 μg of clonidine. The graphs in column e) depict clonidine at 500 μg had no effect on the contralateral sciatic nerve.

FIG. 21 depicts representative compound action potential traces (CAP), sciatic nerve. A stimulating electrode delivered 10 mAMP current to the distal tibial nerve near the internal ankle, and a recording electrode was placed near the proximal sciatic nerve (at the sciatic notch). Following baseline recordings (top row), test solution was injected directly into the sciatic nerve (20 µl volume). Evoked compound action potentials at 3 minutes and approximately 50 minutes post-injection appear in the middle and bottom rows, respectively. The graphs in column a) depict 50 µg of clonidine HCL which had no discernable effect on CAP amplitude. The graphs in column b) depict 100 µg of clonidine which significantly blunted CAP amplitude at 3 minutes. The graphs in column c) depict 200 µg clonidine HCL which virtually eliminated the CAP. The clonidine at 500 µg also reliably eliminated acute evoked CAPs (data not shown). The graphs in column d) depict pre-administration of 1 mg of the potent $\alpha_2$ adrenergic receptor antagonist yohimbine HCL which had no effect on the acute anesthetic-like action of 500 µg of clonidine. The graphs in column e) depict clonidine at 500 µg had no effect on the contralateral sciatic nerve.

Having now generally described the invention, the same may be more readily understood through the following reference to the following examples, which are provided by way of illustration and are not intended to limit the present invention unless specified.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An implantable medical device for reducing or treating acute pain in a patient in need of such treatment, the implantable medical device comprising an imidazoline compound comprising 500 µg of clonidine encapsulated in a liposome, the liposome comprising an interior cavity encapsulating the imidazoline compound, the liposome having a diameter in the range of about 0.1 to about 20 µm, the imidazoline compound being disposed in the implantable medical device in a therapeutically effective amount to provide local anesthesia and nerve block in an amount between 50 µg and 500 µg per day for a period of at least 24 hours after implantation at the target tissue site under the skin of the patient such that a targeted delivery of the clonidine limits diffusion of the clonidine to peripheral nerve endings or a central synapse, wherein the liposome comprises cholesterol, 1, 2-dipalmitoyl-sn-glycero-3 phosphorac-(1-glycerol) (DPPG), 1, 2-dierucoylphosphatidylcholine (DEPC) and tricaprylin.

2. The implantable medical device according to claim 1, wherein the implantable medical device is in the form of a biodegradable depot and the acute pain is post-operative pain.

3. The implantable medical device according to claim 1, wherein the implantable medical device provides local anesthesia and nerve block to the target tissue site which is a dorsal root ganglion, peripheral nerve fiber and/or peripheral nerve root.

4. The implantable medical device according to claim 1, wherein (i) the implantable medical device releases the clonidine over a period of at least 48 hours; or (ii) the clonidine comprises clonidine hydrochloride in an amount of about 20 wt. % to about 80 wt. %.

5. The implantable medical device according to claim 1, wherein the clonidine comprises a salt comprising hydrochloric acid.

6. The implantable medical device according to claim 1, wherein the implantable medical device comprises a pore forming agent in an amount of about 1 wt.% to about 10 wt. % of the implantable medical device.

7. The implantable medical device according to claim 1, wherein the device further comprises a sodium chloride solution such that the clonidine comprises from about 0.5 µg to 10,000 µg per mL of the sodium chloride solution, the cholesterol comprises about 4.7 mg per mL of the sodium chloride solution, the DPPG comprises about 0.9 mg per mL of the sodium chloride solution, the tricaprylin comprises about 2.0 mg per mL of the sodium chloride solution, and the DEPC comprises about 8.2 mg per mL of the sodium chloride solution.

* * * * *